US012152053B2

(12) United States Patent
Boons et al.

(10) Patent No.: US 12,152,053 B2
(45) Date of Patent: *Nov. 26, 2024

(54) OLIGOSACCHARIDE ANALYTICAL STANDARDS

(71) Applicant: UNIVERSITY OF GEORGIA RESEARCH FOUNDATION, INC., Athens, GA (US)

(72) Inventors: Geert-Jan Boons, Athens, GA (US); Anthony Robert Prudden, Athens, GA (US); Lin Liu, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,621

(22) Filed: Aug. 31, 2023

(65) Prior Publication Data

US 2024/0199675 A1 Jun. 20, 2024

Related U.S. Application Data

(63) Continuation of application No. 17/116,706, filed on Dec. 9, 2020, now Pat. No. 11,780,872.

(60) Provisional application No. 62/945,613, filed on Dec. 9, 2019.

(51) Int. Cl.
*C07H 5/06* (2006.01)
*C12P 19/26* (2006.01)
*C12P 19/30* (2006.01)

(52) U.S. Cl.
CPC ............. *C07H 5/06* (2013.01); *C12P 19/26* (2013.01); *C12P 19/305* (2013.01)

(58) Field of Classification Search
None
See application file for complete search history.

(56) References Cited

U.S. PATENT DOCUMENTS 11,780,872 B2 * 10/2023 Boons ................. C12P 19/26
536/53

OTHER PUBLICATIONS

Alexander, S. R., Lim, D., Amso, Z., Brimble, M. A. & Fairbanks, A. J. Protecting group free synthesis of glycosyl thiols from reducing sugars in water; application to the production of N-glycan glycoconjugates. Org. Biomol. Chem. 15, 2152-2156 (2017).
Antonopoulos, A. et al. Loss of effector function of human cytolytic T lymphocytes is accompanied by major alterations in N- and O-glycosylation. J. Biol. Chem. 287, 11240-11251 (2012).
Aoki, D., Appert, H. E., Johnson, D., Wong, S. S. & Fukuda, M. N. Analysis of the substrate binding sites of human galactosyltransferase by protein engineering. EMBO J. 9, 3171-3178 (1990).
Bayley, H., Standring, D. N. & Knowles, J. R. Propane-1,3-dithiol—selective reagent for efficient reduction of alkyl and aryl azides to amines. Tetrahedron Lett. 19, 3633-3634 (1978).
Beckett, D., Kovaleva, E. & Schatz, P. J. A minimal peptide substrate in biotin holoenzyme synthetasecatalyzed biotinylation. Protein Sci. 8, 921-929 (1999).
Cai, L. Recent progress in enzymatic synthesis of sugar nucleotides. J. Carbohydr. Chem. 31, 535-552 (2012).
Calderon, A. D. et al. An enzymatic strategy to asymmetrically branched N-glycans. Org. Biomol. Chem. 15, 7258-7262 (2017).
Carrington, J. C., Cary, S. M., Parks, T. D. & Dougherty, W. G. A second proteinase encoded by a plant potyvirus genome. EMBO J. 8, 365-370 (1989).
Chen, Y. et al. One-pot three-enzyme synthesis of UDP-GlcNAc derivatives. Chem. Commun. 47, 10815-10817 (2011).
Choo, M. et al. Characterization of H type 1 and type 1 N-acetyl-lactosamine glycan epitopes on ovarian cancer specifically recognized by the anti-glycan monoclonal antibody mAb-A4. J. Biol. Chem. 292, 6163-6176 (2017).
Cummings, R. D. & Pierce, J. M. The challenge and promise of glycomics. Chem. Biol. 21, 1-15 (2014).
Cummings, R. D. The repertoire of glycan determinants in the human glycome. Mol. Biosyst. 5, 1087-1104 (2009).
Gagarinov, I. A. et al. Chemoenzymatic approach for the preparation of asymmetric bi-, tri- and tetra-antennary N-glycans from a common precursor. J. Am. Chem. Soc. 139, 1011-1018 (2017).
Goddard-Borger, E. D. & Stick, R. V. An efficient, inexpensive and shelf-stable diazotransfer reagent: imidazole-1-sulfonyl azide hydrochloride. Org. Lett. 9, 3797-3800 (2007).
Hamilton, B. S. et al. A library of chemically defined human N-glycans synthesized from microbial oligosaccharide precursors. Sci. Rep. 7, 15907 (2017).
Hanashima, S., Manabe, S. & Ito, Y. Divergent synthesis of sialylated glycan chains: combined use of polymer support, resin capture-release and chemoenzymatic strategies. Angew. Chem. Int. Ed. 44, 4218-4224 (2005).
Hart, G. W. & Copeland, R. J. Glycomics hits the big time. Cell 143, 672-676 (2010).
Heimburg-Molinaro, J., Song, X., Smith, D. F. & Cummings, R. D. Preparation and analysis of glycan microarrays. Curr. Protoc. Protein Sci. 64, 12.10.11-12.10.29 (2011).
Hofmann, J. & Pagel, K. Glycan analysis by ion mobility-mass spectrometry. Angew. Chem. Int. Ed. 56, 8342-8349 (2017).
Huang, W., Giddens, J., Fan, S. Q., Toonstra, C. & Wang, L. X. Chemoenzymatic glycoengineering of intact IgG antibodies for gain of functions. J. Am. Chem. Soc. 134, 12308-12318 (2012).
Hyun, J. Y., Pai, J. & Shin, I. The glycan microarray story from construction to applications. Acc. Chem. Res. 50, 1069-1078 (2017).
Jonke, S., Liu, K. G. & Schmidt, R. R. Solid-phase oligosaccharide synthesis of a small library of N-glycans. Chem. Eur. J. 12, 1274-1290 (2006).
Kiessling, L. L. & Splain, R. A. Chemical approaches to glycobiology. Annu. Rev. Biochem. 79, 619-653 (2010).
Kizuka, Y. & Taniguchi, N. Enzymes for N-glycan branching and their genetic and nongenetic regulation in cancer. Biomolecules 6, 25 (2016).

(Continued)

*Primary Examiner* — Traviss C McIntosh, III
(74) *Attorney, Agent, or Firm* — Meunier Carlin & Curfman LLC

(57) ABSTRACT

Disclosed herein are oligosaccharides and intermediates useful for the production thereof. The compounds are useful as analytical standards and as intermediates for the preparation of more complex oligosaccharide and N-glycan products. The compounds may be prepared in high purity using the selective stop/go synthetic methods disclosed herein.

16 Claims, 5 Drawing Sheets

(56) References Cited

OTHER PUBLICATIONS

Lauber, M. A., Koza, S. M. & Fountain, K. J. Optimization of GlycoWorks HILIC SPE for the Quantitative and Robust Recovery of N-linked Glycans from mAb-type Samples Waters Application Note 720004717EN (Waters Corporation, Milford, 2013).
Lauc, G., Pezer, M., Rudan, I. & Campbell, H. Mechanisms of disease: the human N-glycome. Biochim. Biophys. Acta 1860, 1574-1582 (2016).
Li, L. et al. Efficient chemoenzymatic synthesis of an N-glycan isomer library. Chem. Sci. 6, 5652-5661 (2015).
Li, T. et al. Divergent chemoenzymatic synthesis of asymmetrical-corefucosylated and core-unmodified N-glycans. Chem. Eur. J. 22, 18742-18746 (2016).
Li, Tiehai, et al. "An automated platform for the enzyme-mediated assembly of complex oligosaccharides." Nature chemistry 11.3 (Feb. 2019): 229-236.
Liu, L., Prudden, A. R., Bosman, G. P. & Boons, G. J. Improved isolation and characterization procedure of sialylglycopeptide from egg yolk powder. Carbohydr. Res. 452, 122-128 (2017).
Maki, Y., Mima, T., Okamoto, R., Izumi, M. & Kajihara, Y. Semisynthesis of complex-type biantennary oligosaccharides containing lactosamine repeating units from a biantennary oligosaccharide isolated from a natural source. J. Org. Chem. 83, 443-451 (2018).
Maki, Y., Okamoto, R., Izumi, M., Murase, T. & Kajihara, Y. Semisynthesis of intact complex-type triantennary oligosaccharides from a biantennary oligosaccharide isolated from a natural source by selective chemical and enzymatic glycosylation. J. Am. Chem. Soc. 138, 3461-3468 (2016).
Masuko, S. et al. Chemoenzymatic synthesis of uridine diphosphate-GlcNAc and uridine diphosphate-GalNAc analogs for the preparation of unnatural glycosaminoglycans. J. Org. Chem. 77, 1449-1456 (2012).
Meng, L. et al. Enzymatic basis for N-glycan sialylation: structure of rat a2,6-sialyltransferase (ST6GAL1) reveals conserved and unique features for glycan sialylation. J. Biol. Chem. 288, 34680-34698 (2013).
Moremen, K. W. et al. Expression system for structural and functional studies of human glycosylation enzymes. Nat. Chem. Biol. 14, 156-162 (2018).
Moremen, K. W., Tiemeyer, M. & Nairn, A. V. Vertebrate protein glycosylation: diversity, synthesis and function. Nat. Rev. Mol. Cell Biol. 13, 448-462 (2012).
Muthana, S., Cao, H. & Chen, X. Recent progress in chemical and chemoenzymatic synthesis of carbohydrates. Curr. Opin. Chem. Biol. 13, 573-581 (2009).
Ohtsubo, K. & Marth, J. D. Glycosylation in cellular mechanisms of health and disease. Cell 126, 855-867 (2006).
Paschinger, K., Staudacher, E., Stemmer, U., Fabini, G. & Wilson, I. B. Fucosyltransferase substrate specificity and the order of fucosylation in invertebrates. Glycobiology 15, 463-474 (2005).
Pedelacq, J. D., Cabantous, S., Tran, T., Terwilliger, T. C. & Waldo, G. S. Engineering and characterization of a superfolder green fluorescent protein. Nat. Biotechnol. 24, 79-88 (2006).
Peng, W. et al. Recent H3N2 viruses have evolved specificity for extended, branched human-type receptors, conferring potential for increased avidity. Cell Host Microbe 21, 23-34 (2017).
Pilobello, K. T. & Mahal, L. K. Deciphering the glycocode: the complexity and analytical challenge of glycomics. Curr. Opin. Chem. Biol. 11, 300-305 (2007).
Prudden, A. R. et al. Synthesis of asymmetrical multiantennary human milk oligosaccharides. Proc. Natl Acad. Sci. USA 114, 6954-6959 (2017).
Schachter, H. & Freeze, H. H. Glycosylation diseases: quo vadis? Biochim. Biophys. Acta 1792, 925-930 (2009).
Schmaltz, R. M., Hanson, S. R. & Wong, C. H. Enzymes in the synthesis of glycoconjugates. Chem. Rev. 111, 4259-4307 (2011).
Seko, A. et al. Occurence of a sialylglycopeptide and free sialylglycans in hen's egg yolk. Biochim. Biophys. Acta 1335, 23-32 (1997).
Serna, S., Etxebarria, J., Ruiz, N., Martin-Lomas, M. & Reichardt, N. C. Construction of N-glycan microarrays by using modular synthesis and on-chip nanoscale enzymatic glycosylation. Chem. Eur. J. 16, 13163-13175 (2010).
Shivatare, S. S. et al. Modular synthesis of N-glycans and arrays for the hetero-ligand binding analysis of HIV antibodies. Nat. Chem. 8, 338-346 (2016).
Stowell, S. R. et al. Galectin-1, -2, and -3 exhibit differential recognition of sialylated glycans and blood group antigens. J. Biol. Chem. 283, 10109-10123 (2008).
Sun, B., Srinivasan, B. & Huang, X. F. Pre-activation-based one-pot synthesis of an $\alpha$-(2,3)-sialylated core-fucosylated complex type bi-antennary N-glycan dodecasaccharide. Chem. Eur. J. 14, 7072-7081 (2008).
Umekawa, M et al. Efficient transfer of sialo-oligosaccharide onto proteins by combined use of a glycosynthase-like mutant of Mucor hiemalis endoglycosidase and synthetic sialo-complex-type sugar oxazoline. Biochim. Biophys. Acta 1800, 1203-1209 (2010).
Unverzagt, C. Chemoenzymatic synthesis of a sialylated undecasaccharide-asparagine conjugate. Angew. Chem. Int. Ed. Engl. 35, 2350-2353 (1996).
Unverzagt, C. et al. Synthesis of multiantennary complex type N-glycans by use of modular building blocks. Chem. Eur. J. 15, 12292-12302 (2009).
Van den Eijnden, D. H., Blanken, W. M. & van Vliet, A. Branch specificity of ß -d-galactosidase from *Eschericha coli*. Carbohydr. Res. 151, 329-335 (1986).
Vandersall-Nairn, A. S., Merkle, R. K., O'Brien, K., Oeltmann, T. N. & Moremen, K. W. Cloning, expression, purification, and characterization of the acid alpha-mannosidase from Trypanosoma cruzi. Glycobiology 8, 1183-1194 (1998).
Voynow, J. A., Kaiser, R. S., Scanlin, T. F. & Glick, M. C. Purification and characterization of GDP-1-fucose-N-acetyl ß -d-glucosaminide al-> 6fucosyltransferase from cultured human skin fibroblasts: equirement of a specific biantennary oligosaccharide as substrate. J. Biol. Chem. 266, 21572-21577 (1991).
Walczak, M. A. & Danishefsky, S. J. Solving the convergence problem in the synthesis of triantennary N-glycan relevant to prostate-specific membrane antigen (PSMA). J. Am. Chem. Soc. 134, 16430-16433 (2012).
Wang, L. X. & Lomino, J. V. Emerging technologies for making glycandefined glycoproteins. ACS Chem. Biol. 7, 110-122 (2012).
Wang, Z. et al. A general strategy for the chemoenzymatic synthesis of asymmetrically branched N-glycans. Science 341, 379-383 (2013).
Xu, Y. et al. Chemoenzymatic synthesis of homogeneous ultralow molecular weight heparins. Science 334, 498-501 (2011).
Zauner, G., Deelder, A. M. & Wuhrer, M. Recent advances in hydrophilic interaction liquid chromatography (HILIC) for structural glycomics. Electrophoresis 32, 3456-3466 (2011).

* cited by examiner

OLIGOSACCHARIDE ANALYTICAL STANDARDS

CROSS-REFERENCE TO RELATED APPLICATIONS

This application is a continuation of U.S. application Ser. No. 17/116,706, filed Dec. 9, 2020, which claims the benefit of U.S. Provisional Application No. 62/945,613, filed Dec. 9, 2019, the contents of which are hereby incorporated in their entirety.

STATEMENT OF GOVERNMENT SUPPORT

This invention was made with government support under P01GM107012, P41GM103390, U01GM120408 and F31CA180478 awarded by the National Institutes of Health. The government has certain rights in the invention.

FIELD OF THE INVENTION

The invention is directed to synthesis of complex N-linked oligosaccharide including methods of preparing key intermediates that can be readily elaborated into more complicated compounds such as glycoconjugates, and derivatives thereof for use as native or isotopically enriched analytical standards with application in mass spectrometry, high-pressure liquid chromatography, capillary electrophoresis, and nuclear magnetic resonance; for antibody, glycoprotein, and therapeutic development; and for construction of analytical or high-throughput platforms including microarray and biofluid analysis.

BACKGROUND

N-glycosylation of proteins is one of the most complex and diverse post-translational modifications that can influence a multitude of biological processes such as signal transduction, embryogenesis, neuronal development, fertilization, hormone activity, immune regulation and the proliferation of cells and their organization into specific tissues. It has been implicated in the etiology of many human diseases such as pathogen recognition, inflammation, immune responses, the development of autoimmune diseases, and cancer. Although it is widely accepted that N-glycans contain high information content, the limited accessibility of well-defined structures makes it difficult to uncover the molecular basis by which they regulate biological and disease processes. Consequently, diverse collections of well-defined N-glycans are needed as standards for glycan structure determination of heterogeneous biological samples, as ligands to study interactions with glycan-binding proteins, as probes to examine the molecular basis of glycoconjugate biosynthesis and as starting materials for glycoprotein synthesis.

There remains a need for improved methods of synthesizing oligosaccharides, including those found in biologically relevant systems, including glycans. There remains a need for analytical standards permitting the rapid identification and quantification of N-glycans in a biomolecule of interest.

FIG. 1 depicts Structure of N-glycans and a bio-inspired strategy for their preparation. FIG. 1a, MGAT enzymes responsible for installing GlcNAc at different branching points. FIG. 1b. Enzyme classes involved in the biosynthesis of complex N-glycans. FIG. 1c. Structure of unnatural UDP-GlcNTFA (4). FIG. 1d, Bio-inspired strategy for the synthesis of asymmetric N-glycans. Symmetrical bi-antennary glycan 1, which can easily be obtained from a glycopeptide isolated from egg yolk, can be further branched by recombinant MGAT4 and MGAT5. The use of unnatural UDP-GlcNTFA makes it possible to prepare 2 bearing GlcNAc, GlcN$_3$ and GlcNH$_2$ branching moieties. Compound 2 is the key intermediate for preparing complex targets such as 3. FIG. 1e, Transformation of GlcNTFA, installed by MGAT4 and MGAT5, into GlcNH$_2$ or GlcN$_3$ 'stops' further enzymatic extension of these moieties until they are converted into natural GlcNAc ('go'), which can then be elaborated by glycosyltransferases into complex appendages. FIG. 2 depicts the synthesis of asymmetric branched tri-antennary glycosyl asparagines using MGAt5 and uDP-GlcNtFA. MGAT5 readily accepts UDP-GlcNTFA to give a tri-antennary glycan that, following base treatment, provides a compound with a GlcNH$_2$ at the β6 arm. The latter residue is not a substrate for the galactosyl transferase B4GalT1 and therefore it is possible to selectively elaborate the MGAT1 and MGAT2 arms by exploiting the inherent branch selectivities of glycosidases and glycosyltransferases. Once the MGAT1 and MGAT2 arms were capped with Neu5Ac, preventing these positions from further elongation, the GlcNH$_2$ could be acetylated to give natural GlcNAc capable of being extended by a series of glycosyltransferases. FIG. 3 depicts the synthesis of asymmetric branched tetra-antennary N-glycans using MGAt4 and MGAt5 in combination with uDP-GlcNtFA and subsequent conversion of the transferred GlcNtFA into GlcN$_3$ or GlcNH$_2$. The latter moieties are temporarily disabled from modification by glycosyltransferases, making it possible to selectively elaborate the MGAT1 and MGAT2 arms. At an appropriate point in the synthesis, the unnatural GlcN$_3$ or GlcNH$_2$ moieties can be converted into natural GlcNAc, allowing each arm to be uniquely extended.

DETAILED DESCRIPTION

Figure 1:
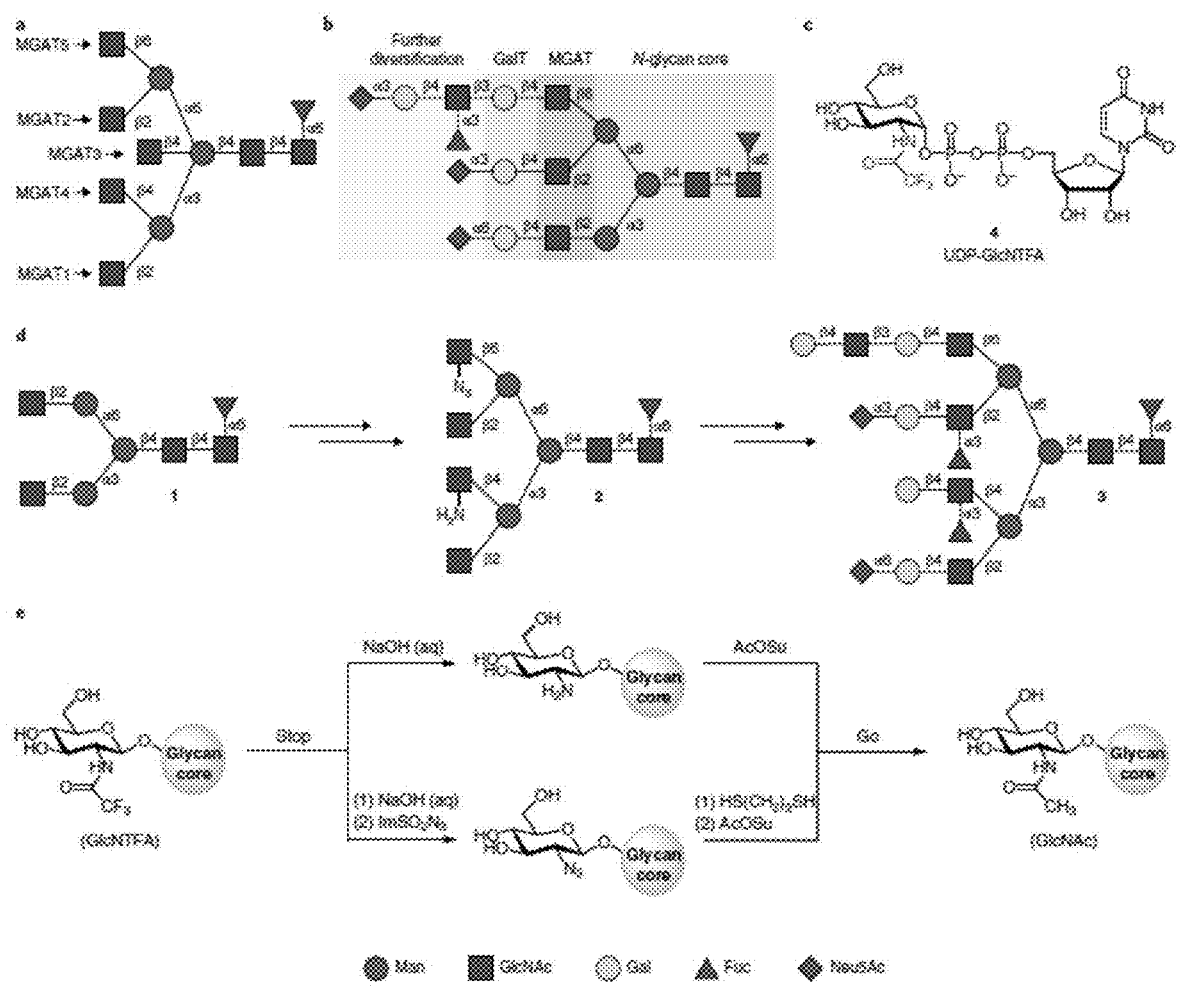
Figure 2:
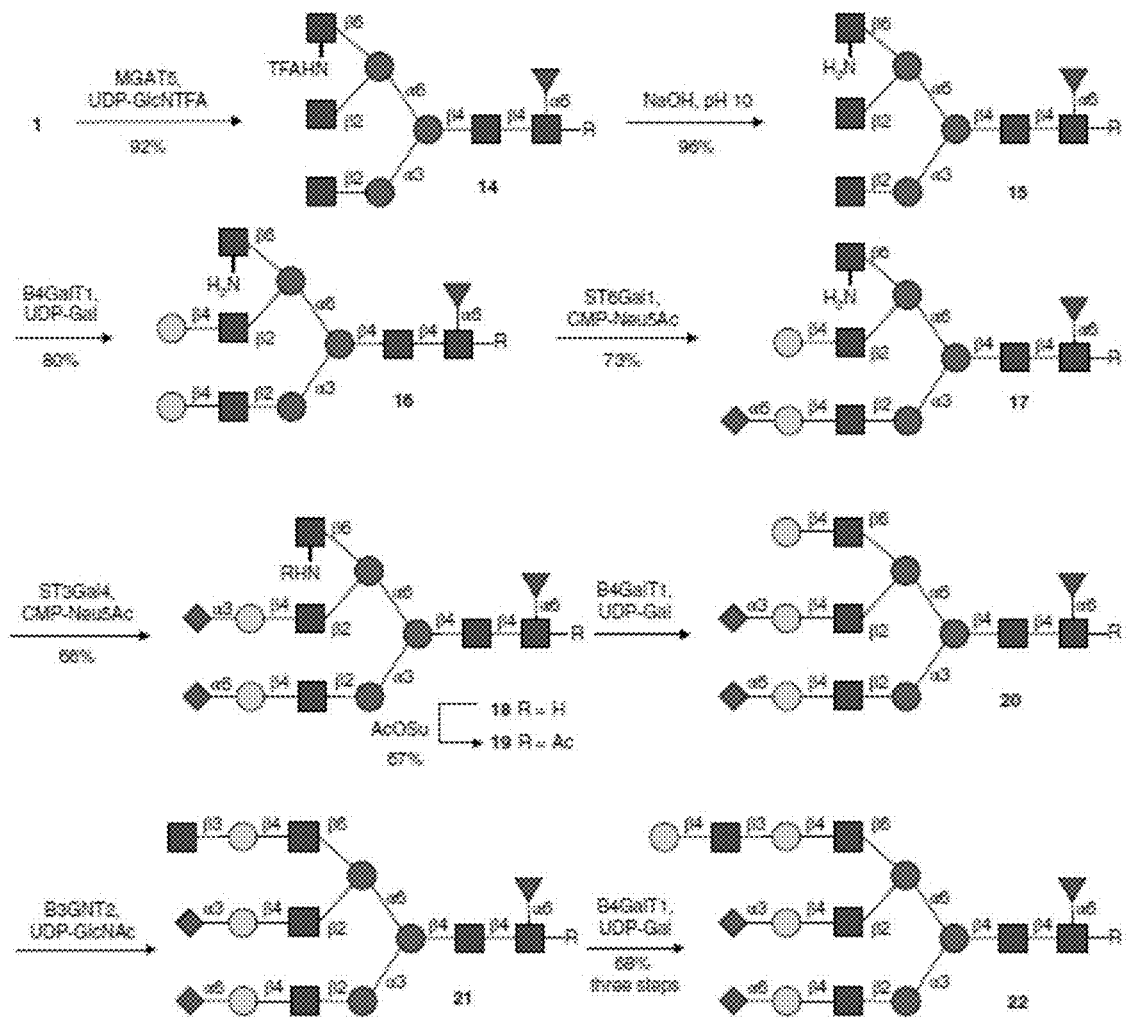
Figure 3:
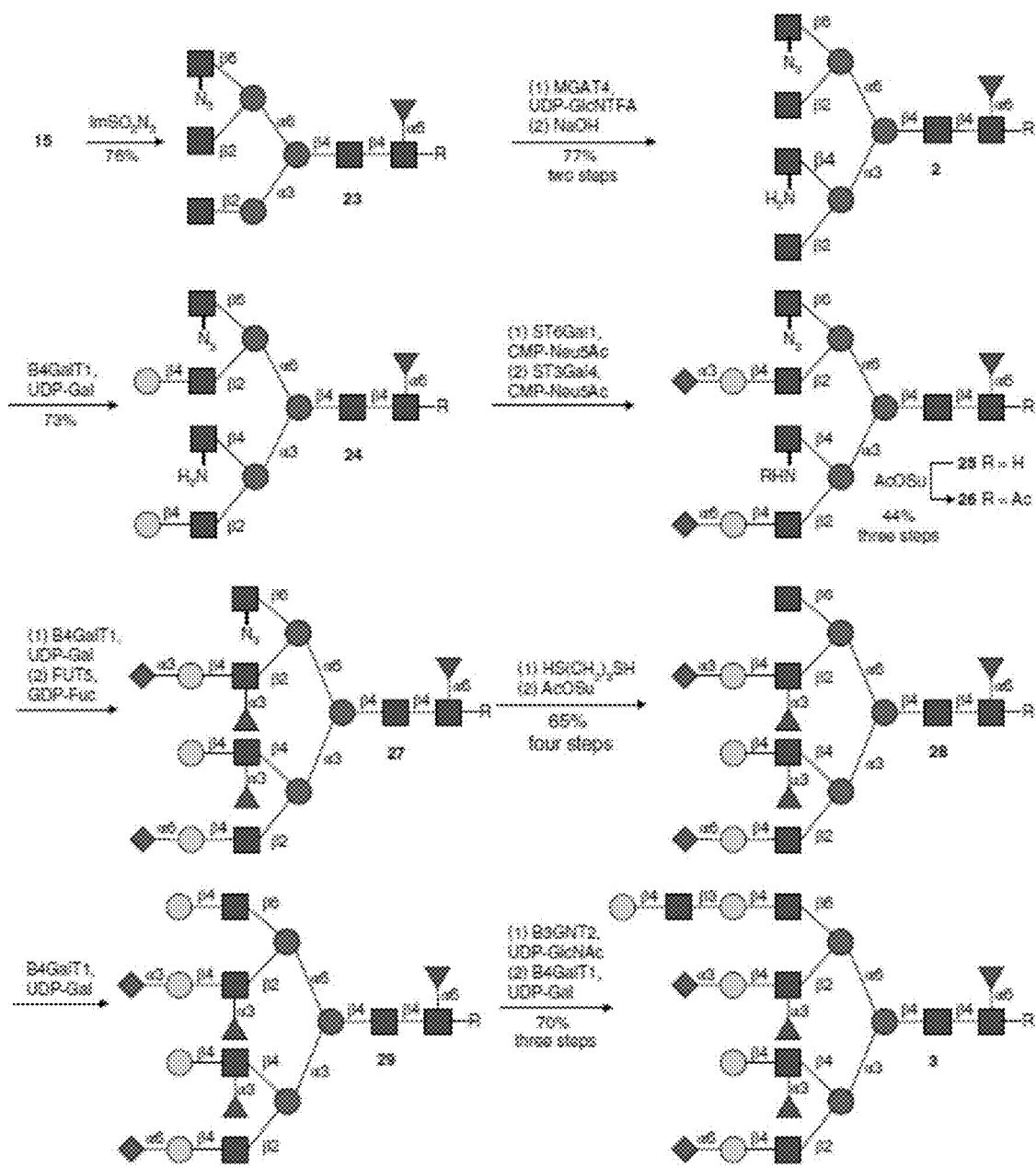
Figure 4:
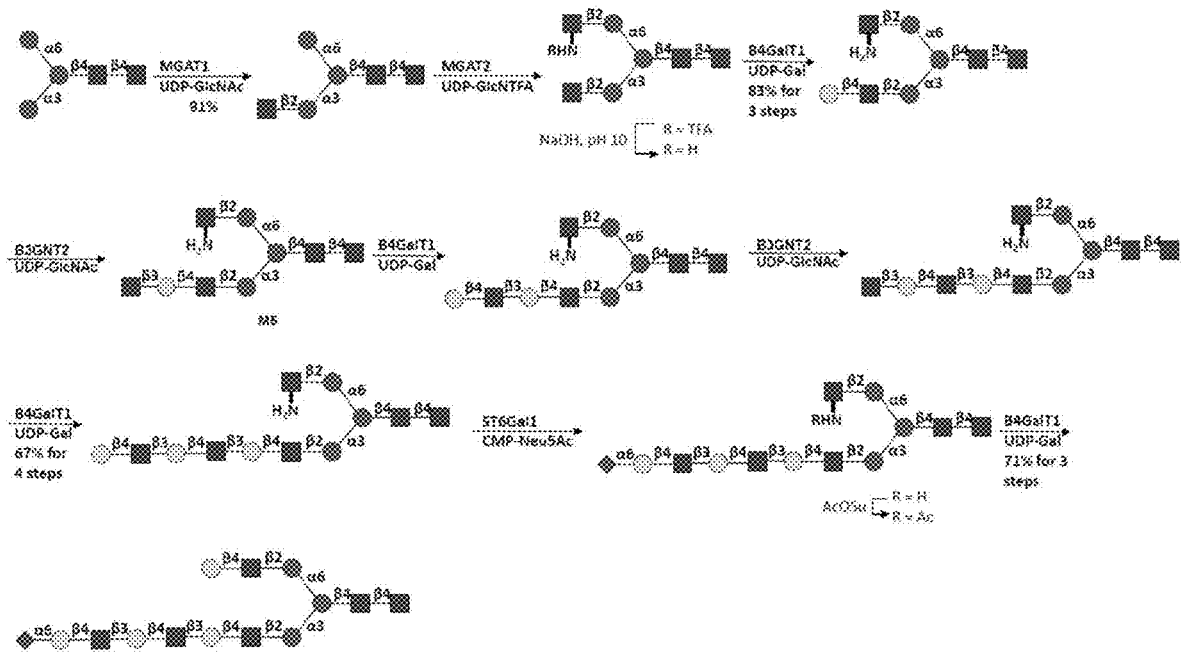
FIG. 4 depicts additional compounds of the invention. The symbols used to depict sugars is presented in FIG. 1.
Figure 5:
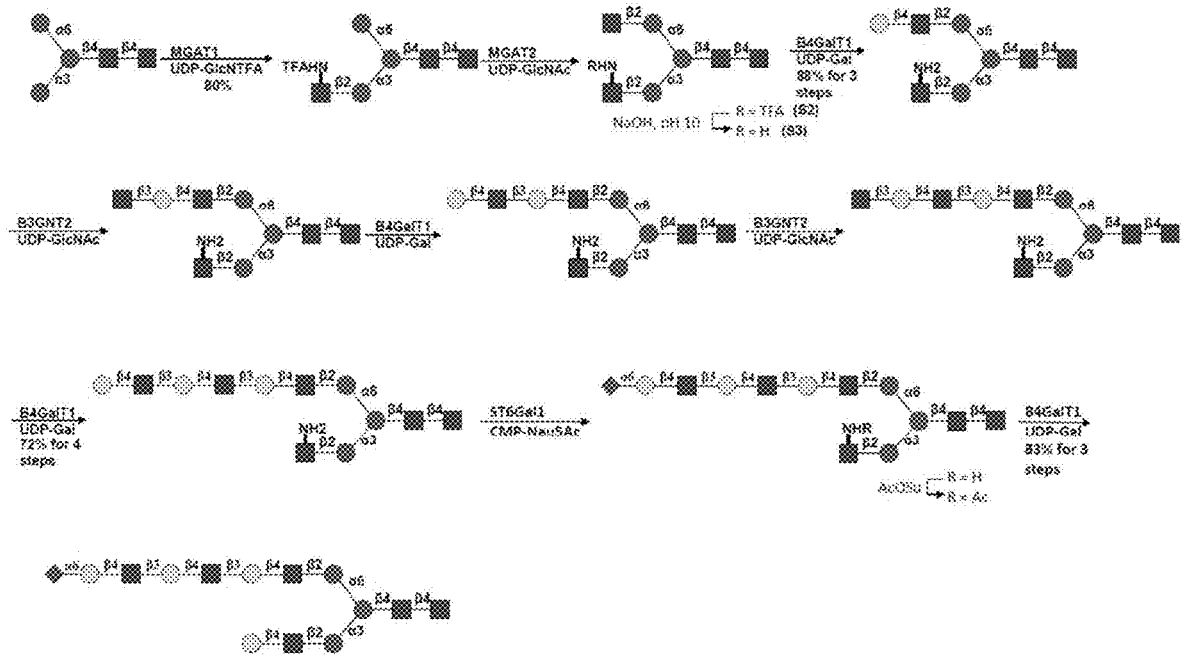
FIG. 5 depicts additional compounds of the invention. The symbols used to depict sugars is presented in FIG. 1.
Figure 6:
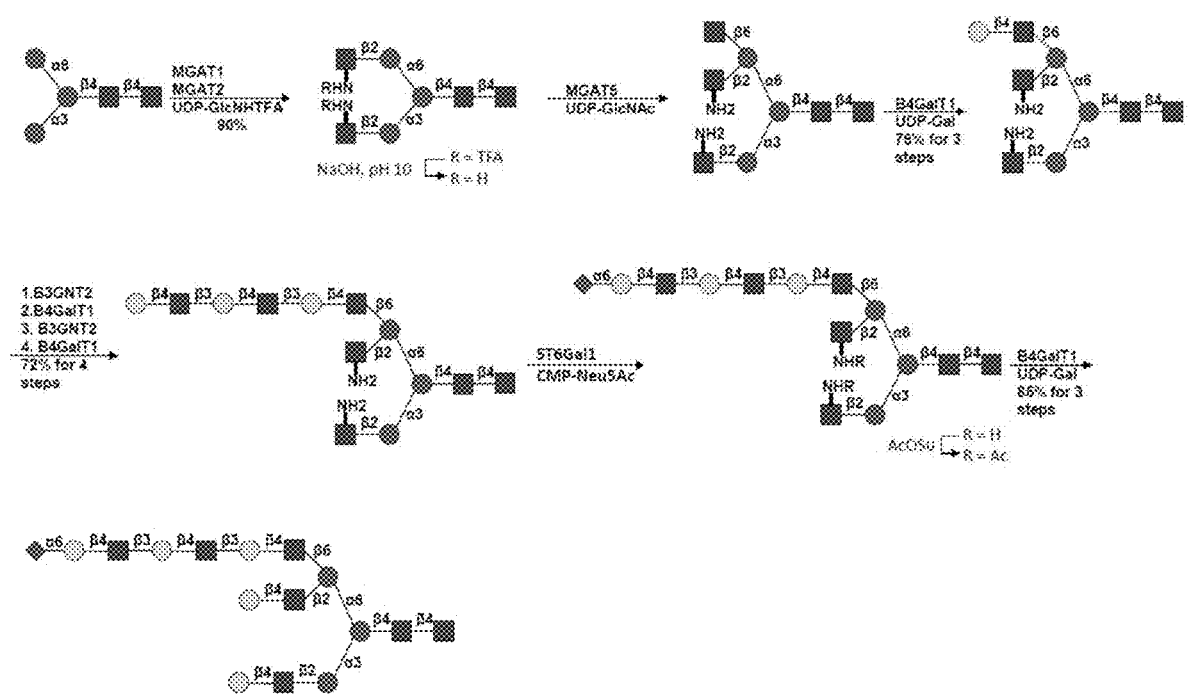
FIG. 6 depicts additional compounds of the invention. The symbols used to depict sugars is presented in FIG. 1.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about." it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps.

"Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

The term "cycloalkyl" as used herein is a non-aromatic carbon-based ring composed of at least three carbon atoms. Examples of cycloalkyl groups include, but are not limited to cyclopropyl, cyclobutyl, cyclopentyl, cyclohexyl, etc. The term "heterocycloalkyl" is a cycloalkyl group as defined above where at least one of the carbon atoms of the ring is replaced with a heteroatom such as, but not limited to, nitrogen, oxygen, sulfur, selenium or phosphorus. The cycloalkyl group and heterocycloalkyl group can be substituted or unsubstituted. Unless stated otherwise, the terms "cycloalkyl" and "heterocycloalkyl" contemplate both substituted and unsubstituted cyloalkyl and heterocycloalkyl groups. The cycloalkyl group and heterocycloalkyl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. A cycloalkyl group which contains no double or triple carbon-carbon bonds is designated a saturated cycloalkyl group, whereas a cycloalkyl group having one or more such bonds (yet is still not aromatic) is designated an unsaturated cycloalkyl group. Unless specified to the contrary, the term cycloalkyl embraces both saturated and unsaturated, non-aromatic, ring systems.

The term "aryl" as used herein is an aromatic ring composed of carbon atoms. Examples of aryl groups include, but are not limited to, phenyl and naphthyl, etc. The term "heteroaryl" is an aryl group as defined above where at least one of the carbon atoms of the ring is replaced with a heteroatom such as, but not limited to, nitrogen, oxygen, sulfur, selenium or phosphorus. The aryl group and heteroaryl group can be substituted or unsubstituted. Unless stated otherwise, the terms "aryl" and "heteroaryl" contemplate both substituted and unsubstituted aryl and heteroaryl groups. The aryl group and heteroaryl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol.

Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cirrnolinyl, decahydroquinolinyl, 2H,6H~1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The terms "alkoxy." "cycloalkoxy," "heterocycloalkoxy," "cycloalkoxy," "aryloxy," and "heteroaryloxy" have the aforementioned meanings for alkyl, cycloalkyl, heterocycloalkyl, aryl and heteroaryl, further providing said group is connected via an oxygen atom.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent can be substituted with one or more of the following: alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. In a specific example, groups that are said to be substituted are substituted with a protic group, which is a group that can be protonated or deprotonated, depending on the pH.

The skilled person will understand that when the disclosed compounds bear ionizable functional groups (e.g., amines, carboxylic acids, sulfonic acids, etc) the compounds may be protonated or deprotonated depending on pH. Unless specifically stated otherwise, the structure of a compound embraces all ionized forms of the compound as well. Acceptable salts of the disclosed compounds may be formed under conventional conditions. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate.

Disclosed herein are a family of oligosaccharides and intermediates useful as analytical standards, and for applications such as glycopeptide synthesis, microarray development, and others. The oligosaccharides can have the formula:

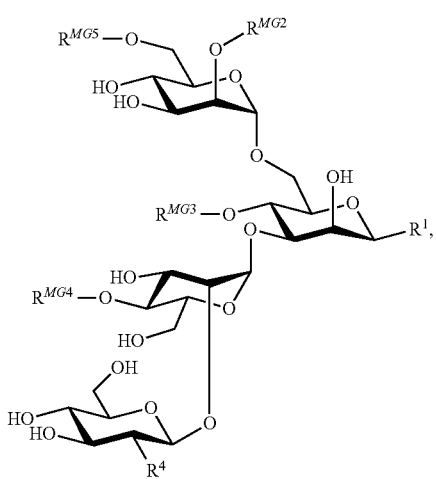

wherein $R^1$ and $R^4$ are as defined herein, $R^{MG2}$, $R^{MG3}$, $R^{MG4}$, and $R^{MG5}$, are each independently chosen from H, GlcNAc, or modified GlcNAc. As used herein, a modified GlcNAc refers to a 2-deoxygluco residue bearing substituted or unsubstituted nitrogen atom at the 2-position.

In some embodiments, the invention relates to a modified GlcNAc glycosyl donor having the formula:

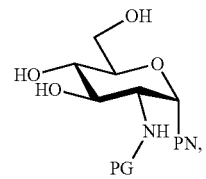

wherein PN represents a phosphonucleotide and PG represents a protective group that is tolerated by glycosyltransferase enzymes. After glycosylation, the protective group can be removed to yield the corresponding 2-deoxyglucosamine, which can be further derivatized using appropriate chemistries. Because the 2-deoxyglucosamine and derivatives thereof are not substrates for galactosyltransferase, the present invention provides methods of selectively preparing a vast number of different oligosaccharide compounds.

Disclosed herein are oligosaccharide compounds having the formula:

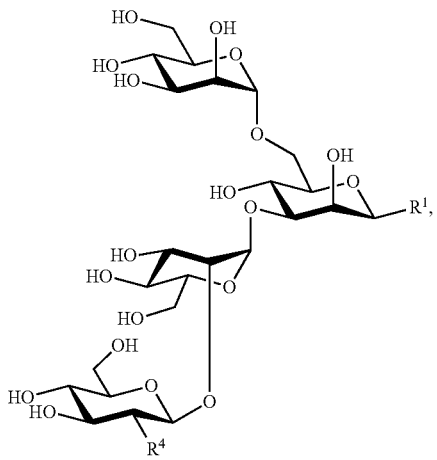

and salts thereof, wherein
$R^1$ can be OH, or a residue having the formula:

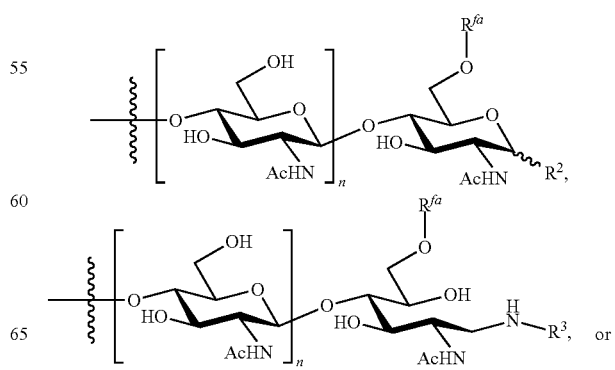

-continued

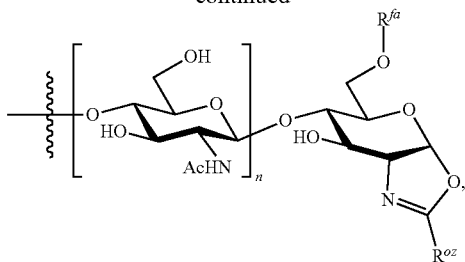

wherein $R^{oz}$ can be H, $C_{1-4}$alkyl (preferably $CH_3$), aryl, $CF_3$, $CCl_3$, n can be 1 or 0;

$R^{fa}$ can be H or a fucose residue having the structure:

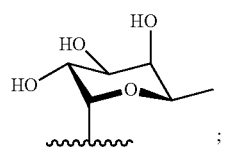

$R^2$ can be $OR^c$, $NR^{2n}OR^c$; $NR^{2n}R^c$ and $R^3$ can be $OR^c$ or $R^c$;

wherein:

$R^{2n}$ can be H and $C_{1-4}$alkyl;

$R^c$ can be $X^pH$, $X^pC_{1-8}$alkyl, $X^pC_{1-8}$alkylaryl, $X^p$aryl, $X^p$fluorescent marker, or an amino acid residue having the formula:

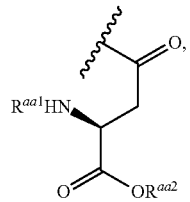

wherein $R^{aa1}$ and $R^{aa2}$ can be H or additional amino acid residues, for instance as found in a protein, polypeptide, monoclonal antibody, etc. In certain embodiments, $R^{aa1}$ can be Cbz (carboxybenzyl ether), and $R^{aa2}$ can be H.

$R^3$ can be $X^pC_{1-8}$alkyl, $X^pC_{1-8}$alkylaryl, or $X^p$aryl;

wherein $X^p$ can be null or a polymer, preferably a polyethylene glycol $—(CH_2CH_2O)_z—$, wherein z is 1-500.

$R^4$ can be $N_3$, $NR^{4a}R^{4b}$, wherein:

$R^{4a}$ and $R^{4b}$ are the same or different, and can be H, $Z—X^4$ wherein Z can be null, C=O, $SO_2$, and $X^4$ can be $C_{1-4}$alkyl, $O—C_{1-4}$alkyl, $C_{1-4}$haloalkyl, $O—C_{1-4}$haloalkyl, $C_{1-4}$alkylaryl, $O—C_{1-4}$alkylaryl, aryl, O-aryl; or $R^{4a}$ and $R^{4b}$ can together form a ring; or $R^4$ can be a radical having the formula:

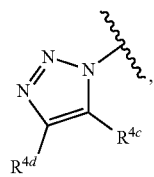

and one or both of $R^{4c}$ or $R^{4d}$ constitute a conjugated payload.

In certain embodiments, $R^{4a}$ can be H and $R^{4b}$ can be methoxymethyl, methylthiomethyl, p-methoxybenzyloxymethyl, p-nitrobenzyloxymethyl, t-butoxymethyl, 2-methoxyethoxymethyl, 1-ethoxyethyl, allyl, p-methoxybenzyloxycarbonyl (Moz), p-nitrobenzyloxycarbonyl (PNZ), trimethylsilyl, diethylisopropylsilyl, triphenylsilyl, formyl, chloroacetyl, methanesulfonyl, tosyl, benzylsulfonyl, methoxymethylcarbonyl, benzyloxycarbonyl, carboxybenzyl (Cbz), t-butyloxycarbonyl (BOC), 9-fluorenylmethylcarbonyl, N-phenylcarbamoyl, [2-(trimethylsilyl)ethoxy]methyl, or 4,4'-dimethoxytrityl.

While $R^2$, when present, can be in either the α or β configuration, or as a mixture of anomers, it is be preferred that $R^2$ is in the β configuration:

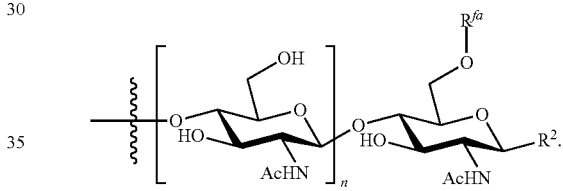

In some instances, n can be zero, e.g., $R^1$ is a residue having the formula:

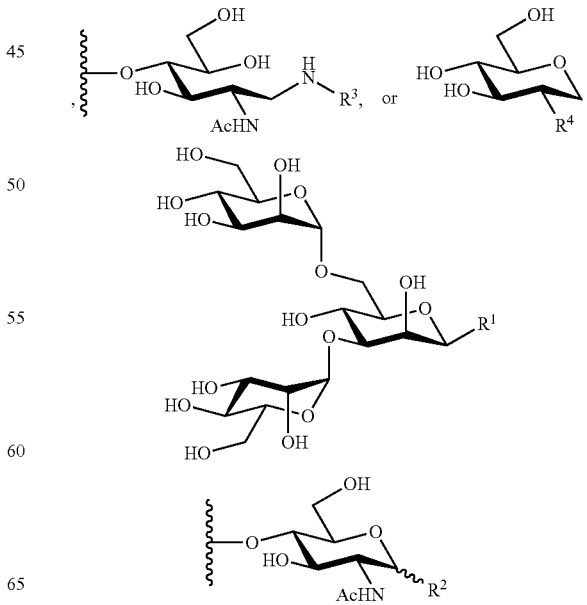

-continued

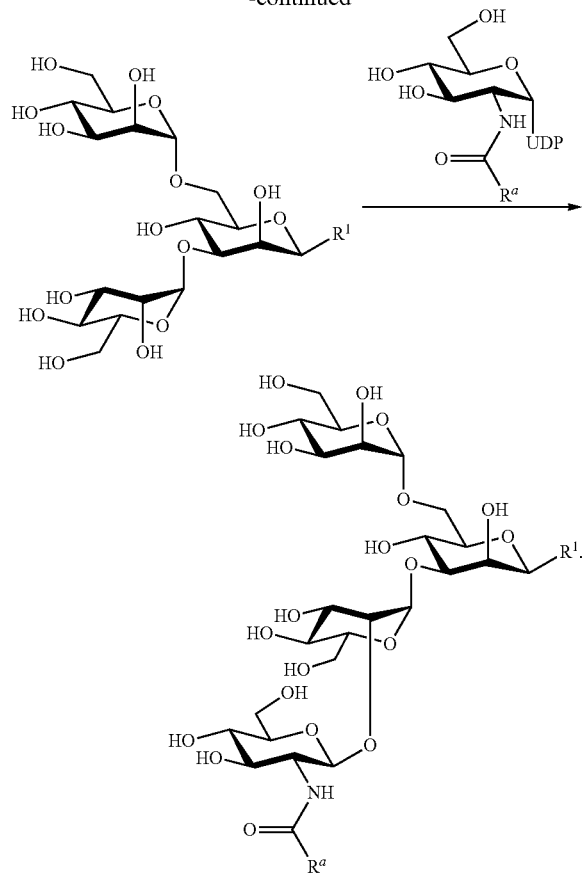

In other embodiments, n is one, e.g., $R^1$ is a residue having the formula:

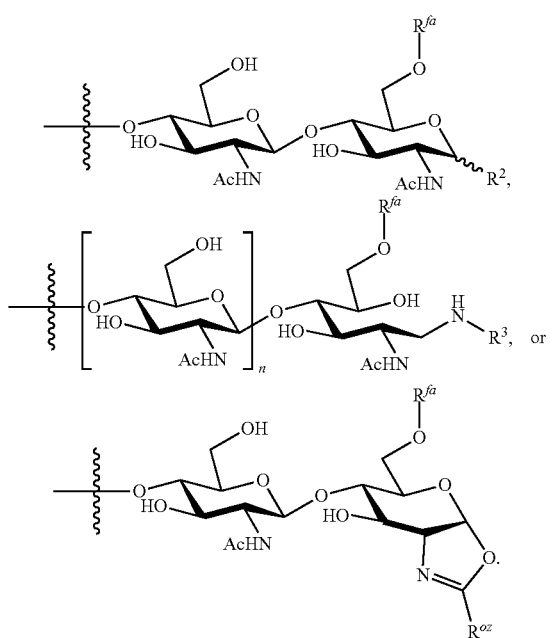

In some instances, $R^c$ can be $C_{1-8}$alkyl, $C_{1-8}$alkylaryl, a polymer such as polyethylene glycol, or aryl bearing functional group enabling covalent or affinity-based immobilization for a microarray slide. For instance, $R^c$ can have the formula $-(CH_2)_{nc}R^{im}$, wherein nc is an integer from 1-8, and $R^{im}$ can be $-NH_2$, $-SH$, $-OH$, $-COOH$, $-N_3$, C≡CH, a Michael acceptor such as vinyl sulfone or maleimide, $SO_3$, $OSO_3$, or a biotin residue having the formula:

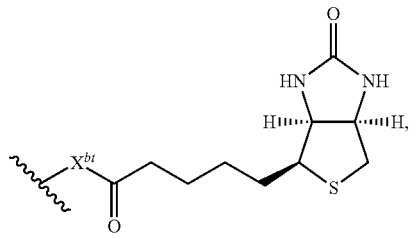

wherein $X^{bt}$ is selected from null, O, NH, or S.

In other instances, $R^c$ can be a group suitable for UV-VIS or fluorescent detection. Suitable aryl groups typically include polyaromatic systems such as coumarins, rhodamines, fluoresceins, cyanines, eosins, erythrosins, and the like.

In other instances, $R^c$ can be a $C_{1-8}$alkylaryl or aryl group suitable for solid phase extractions. Exemplary aryl groups include phenyls and naphthyls bearing two or more sulfonate residues:

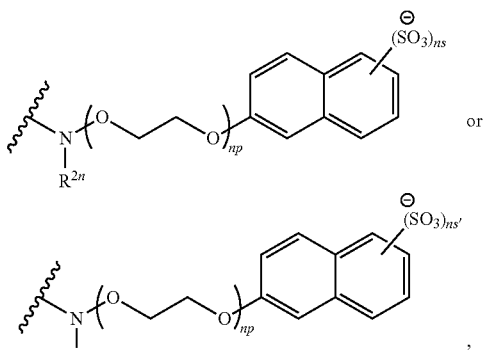

wherein np is from 0-50, ns is from 2-7, and ns' is from 2-5, with two sulfonate groups in an ortho configuration being particularly preferred:

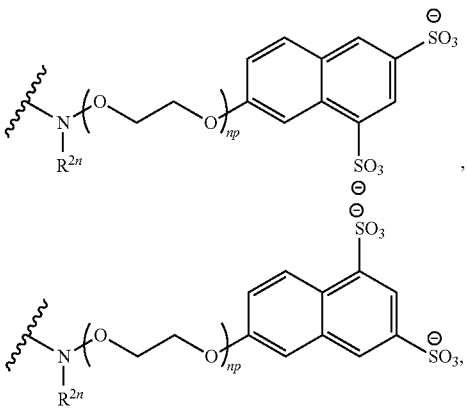

-continued

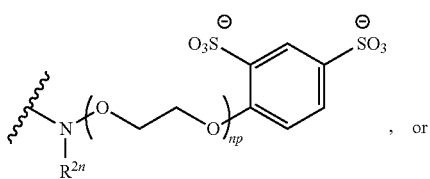

, or

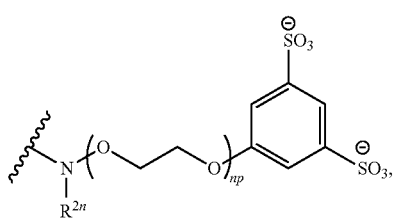

In some embodiments, $R^c$ can be an aryl group useful as a tag is LC-MS, microarray, or capillary electrophoresis analysis. For example $R^c$ can be an aryl (e.g., phenyl, naphthyl, anthracene, phenanthrene, phenalene, tetracene, chrysene, triphenylene, pyrene and the like) residue substituted one or more times by carboxylic acids, carboxamides (especially primary carboxamides), sulfonates, reporter groups such as quaternary ammonium salts and the like. By way of example, suitable tags include residues having the formula:

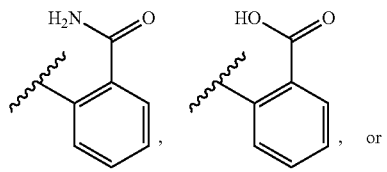

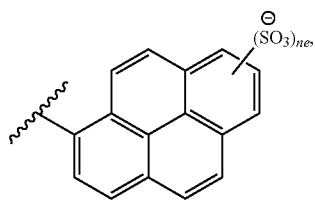

wherein ne is from 2-8.

Also disclosed herein are oligosaccharides having the formula:

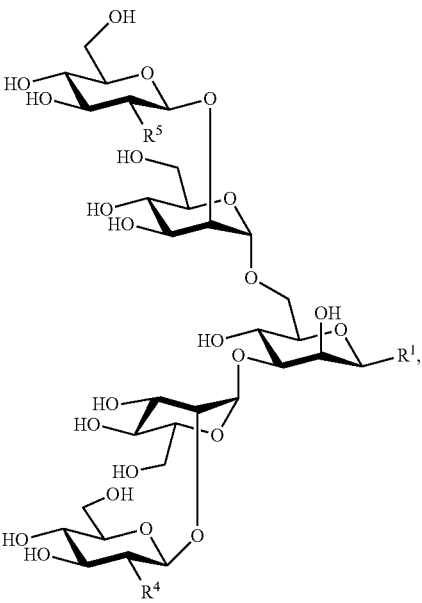

wherein $R^1$ and $R^4$ are as defined above, and $R^5$ can be $N_3$, $NR^{5a}R^{5b}$, wherein $R^{5a}$ and $R^{5b}$ are the same or different, and can be H, Z—$X^5$ wherein Z can be null, C=O, $SO_2$, and $X^4$ can be $C_{1-4}$alkyl, O—$C_{1-4}$alkyl, $C_{1-4}$haloalkyl, O—$C_{1-4}$haloalkyl, $C_{1-4}$alkylaryl, O—$C_{1-4}$alkylaryl, aryl, O-aryl; or $R^{5a}$ and $R^{5b}$ can together form a ring; or $R^5$ can be a radical having the formula:

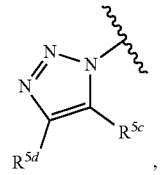

wherein one or both of $R^{5c}$ or $R^{5d}$ constitute a conjugated payload.

In certain embodiments, $R^{5a}$ can be H and $R^{5b}$ can be methoxymethyl, methylthiomethyl, p-methoxybenzyloxymethyl, p-nitrobenzyloxymethyl, t-butoxymethyl, 2-methoxyethoxymethyl, 1-ethoxyethyl, allyl, p-methoxybenzyloxycarbonyl (Moz), p-nitrobenzyloxycarbonyl (PNZ), trimethylsilyl, diethylisopropylsilyl, triphenylsilyl, formyl, chloroacetyl, methanesulfonyl, tosyl, benzylsulfonyl, methoxymethylcarbonyl, benzyloxycarbonyl, carboxybenzyl (Cbz), t-butyloxycarbonyl (BOC), 9-fluorenylmethylcarbonyl, N-phenylcarbamoyl. [2-(trimethylsilyl)ethoxy]methyl, or 4,4'-dimethoxytrityl.

In certain embodiments, the $R^5$ bearing residue can be an isotopically enriched GlcNAc or modified GlcNAc, for instance in which one or more of the carbon atoms are enriched with $^{13}C$ above naturally occurring levels. In some embodiments, $R^5$ bearing residue is a $^{13}C_6$ enriched residue, which herein means that each of the ring carbons and the C-6 carbon are enriched with $^{13}C$ above naturally occurring levels. When $R^5$ is $NHCOCH_3$, one or both of those carbon atoms may also be $^{13}C$ enriched. Such residues are termed $^{13}C_7$ and $^{13}C_8$ enriched residues, respectively. The isotopic enrichment can be at least 90%, at least 95%, at least 98%, or at least 99%.

Also disclosed herein are oligosaccharides having the formula:

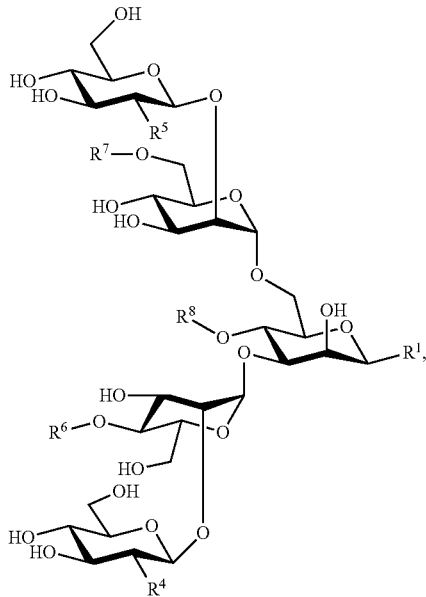

wherein $R^1$, $R^4$, and $R^5$ are as defined above;
$R^6$ can be hydrogen or a residue having the formula:

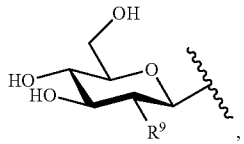

wherein $R^9$ can be $N_3$, $NR^{9a}R^{9b}$, wherein $R^{9a}$ and $R^{9b}$ are the same or different, and can be H, Z—$X^9$ wherein Z can be null, C=O, $SO_2$, and $X^9$ can be $C_{1-4}$alkyl, O—$C_{1-4}$alkyl, $C_{1-4}$haloalkyl, O—$C_{1-4}$haloalkyl, $C_{1-4}$alkylaryl, O—$C_{1-4}$alkylaryl, aryl, O-aryl; or $R^{9a}$ and $R^{9b}$ can together form a ring; or
$R^9$ can be a radical having the formula:

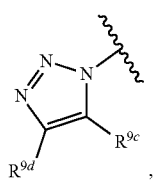

wherein one or both of $R^{9c}$ or $R^{9d}$ constitute a conjugated payload.

In certain embodiments, $R^{9a}$ can be H and $R^{9b}$ can be methoxymethyl, methylthiomethyl, p-methoxybenzyloxymethyl, p-nitrobenzyloxymethyl, t-butoxymethyl, 2-methoxyethoxymethyl, 1-ethoxyethyl, allyl, p-methoxybenzyloxycarbonyl (Moz), p-nitrobenzyloxycarbonyl (PNZ), trimethylsilyl, diethylisopropylsilyl, triphenylsilyl, formyl, chloroacetyl, methanesulfonyl, tosyl, benzylsulfonyl, methoxymethylcarbonyl, benzyloxycarbonyl, carboxybenzyl (Cbz), t-butyloxycarbonyl (BOC), 9-fluorenylmethylcarbonyl, N-phenylcarbamoyl, [2-(trimethylsilyl)ethoxy]methyl, or 4,4'-dimethoxytrityl.

$R^7$ can be hydrogen or a residue having the formula:

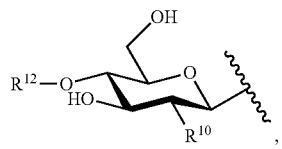

wherein $R^{10}$ can be $N_3$, $NR^{10a}R^{10b}$, wherein $R^{10a}$ and $R^{10b}$ are the same or different, and can be H, Z—$X^{10}$ wherein Z can be null, C=O, $SO_2$, and $X^4$ can be $C_{1-4}$alkyl, O—$C_{1-4}$alkyl, $C_{1-4}$haloalkyl, O—$C_{1-4}$haloalkyl, $C_{1-4}$alkylaryl, O—$C_{1-4}$alkylaryl, aryl, O-aryl; or $R^{10a}$ and $R^{10b}$ can together form a ring; or $R^{10}$ can be a radical having the formula:

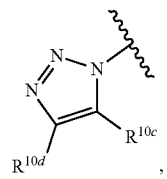

wherein one or both of $R^{10c}$ or $R^{10d}$ constitute a conjugated payload.

In certain embodiments, $R^{10a}$ can be H and $R^{10b}$ can be methoxymethyl, methylthiomethyl, p-methoxybenzyloxymethyl, p-nitrobenzyloxymethyl, t-butoxymethyl, 2-methoxyethoxymethyl, 1-ethoxyethyl, allyl, p-methoxybenzyloxycarbonyl (Moz), p-nitrobenzyloxycarbonyl (PNZ), trimethylsilyl, diethylisopropylsilyl, triphenylsilyl, formyl, chloroacetyl, methanesulfonyl, tosyl, benzylsulfonyl, methoxymethylcarbonyl, benzyloxycarbonyl, carboxybenzyl (Cbz), t-butyloxycarbonyl (BOC), 9-fluorenylmethylcarbonyl, N-phenylcarbamoyl, [2-(trimethylsilyl)ethoxy]methyl, or 4,4'-dimethoxytrityl.

$R^{12}$ can be hydrogen or a residue having the formula:

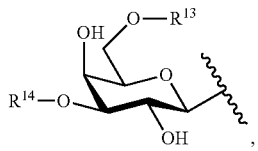

wherein $R^{13}$ can be hydrogen or a residue having the formula:

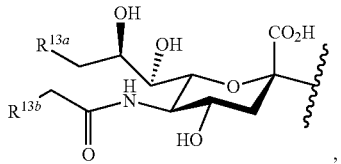

wherein $R^{13b}$ is selected from H and a conjugated cargo moiety, and $R^{13a}$ is selected from OH and a conjugated cargo moiety;

$R^{14}$ can be hydrogen or a residue having the formula:

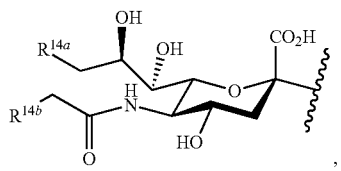

wherein $R^{14b}$ is selected from H and a conjugated cargo moiety, and $R^{14a}$ is selected from OH and a conjugated cargo moiety;

$R^8$ can be hydrogen or a residue having the formula:

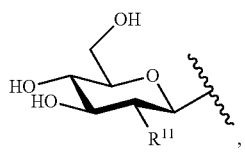

wherein $R^{11}$ can be $N_3$, $NR^{11a}R^{11b}$, wherein $R^{11a}$ and $R^{11b}$ are the same or different, and can be H, Z—$X^{11}$ wherein Z can be null, C=O, $SO_2$, and $X^{11}$ can be $C_{1-4}$alkyl, O—$C_{1-4}$alkyl, $C_{1-4}$haloalkyl, O—$C_{1-4}$haloalkyl, $C_{1-4}$alkylaryl, O—$C_{1-4}$alkylaryl, aryl, O-aryl; or $R^{11a}$ and $R^{11b}$ can together form a ring; or $R^{11}$ can be a radical having the formula:

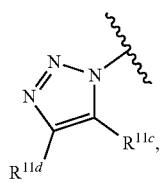

wherein one or both of $R^{11c}$ or $R^{11d}$ constitute a conjugated payload.

In certain embodiments, $R^{11a}$ can be H and $R^{11b}$ can be methoxymethyl, methylthiomethyl, p-methoxybenzyloxymethyl, p-nitrobenzyloxymethyl, t-butoxymethyl, 2-methoxyethoxymethyl, 1-ethoxyethyl, allyl, p-methoxybenzyloxycarbonyl (Moz), p-nitrobenzyloxycarbonyl (PNZ), trimethylsilyl, diethylisopropylsilyl, triphenylsilyl, formyl, chloroacetyl, methanesulfonyl, tosyl, benzylsulfonyl, methoxymethylcarbonyl, benzyloxycarbonyl, carboxybenzyl (Cbz), t-butyloxycarbonyl (BOC), 9-fluorenylmethylcarbonyl, N-phenylcarbamoyl, [2-(trimethylsilyl)ethoxy]methyl, or 4,4'-dimethoxytrityl.

Disclosed herein are oligosaccharides having the formula:

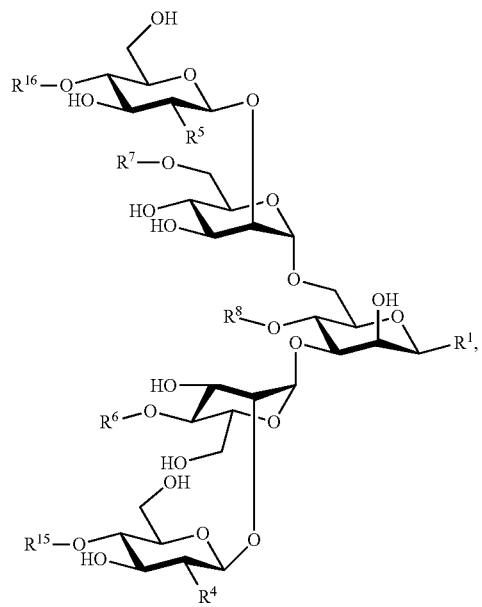

wherein $R^1$, $R^4$, $R^5$, $R^6$, $R^7$, and $R^8$ have the meanings given above;

$R^{15}$ can hydrogen or a residue having the formula:

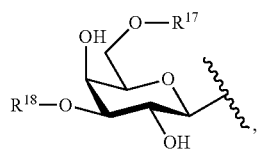

wherein $R^{17}$ can be hydrogen or a residue having the formula:

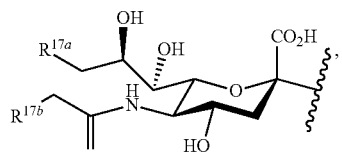

wherein $R^{17b}$ can be H or a conjugated cargo moiety, and $R^{17a}$ can be OH or a conjugated cargo moiety;

$R^{18}$ can be hydrogen or a residue having the formula:

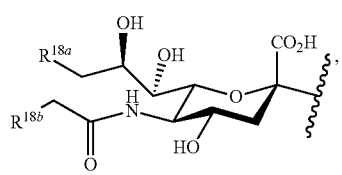

wherein $R^{18b}$ is can be H or a conjugated cargo moiety, and $R^{18a}$ can be OH or a conjugated cargo moiety;

$R^{16}$ can be hydrogen or a residue having the formula:

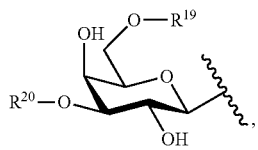

wherein $R^{19}$ can be hydrogen or a residue having the formula:

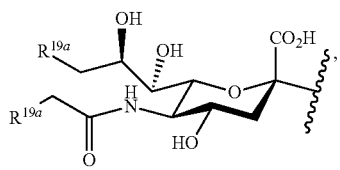

wherein $R^{18b}$ can be H or a conjugated cargo moiety, and $R^{18a}$ can be OH or a conjugated cargo moiety;

$R^{20}$ can be hydrogen or a residue having the formula:

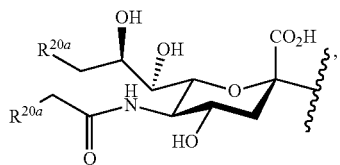

wherein $R^{20b}$ can be H or a conjugated cargo moiety, and $R^{20a}$ can be OH and a conjugated cargo moiety.

As used herein, a conjugated payload in the context of the triazole residues described above can be formed using click chemistry cycloadditions between an azide and alkyl or alkene:

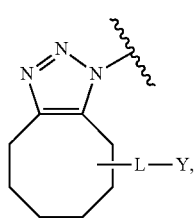

wherein Y is a cytotoxic drug or tracer compound, and L is a linker. In some instances the conjugated payload/triazole can have the formula:

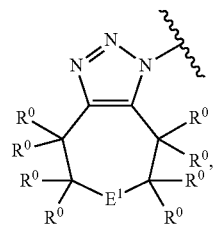

wherein $R^0$ is in each case independently selected from hydrogen, halogen, $C_{1-8}$alkyl, $C_{1-8}$alkoxy, aryl, $C_{1-8}$heteroaryl, $C_{3-8}$cycloalkyl, or $C_{1-8}$heterocyclyl; wherein any two or more $R^0$ groups can together form a ring;

$E^1$ can be:

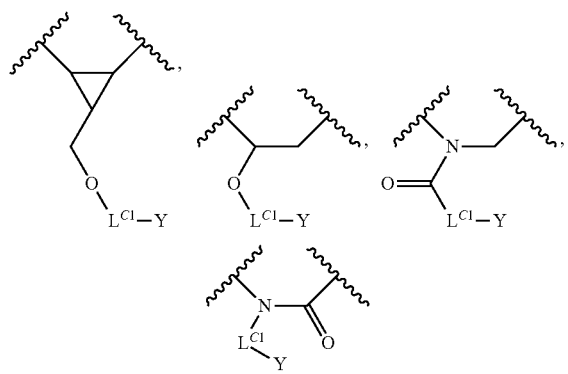

wherein $L^{C1}$ can be null, cleavable linker, and non-cleavable linker. In some embodiments, the conjugated payload/triazole can have the formula:

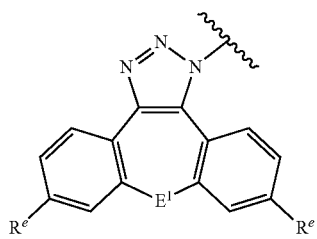

wherein $R^e$ is selected from hydrogen, or either *—$OSO_3X^1$ or *—$OPO_3X_1$, wherein $X_1$ is selected from H, $C_{1-8}$alkyl, or a pharmaceutically acceptable cation. In other embodiments, each of $R^0$ is hydrogen.

Compounds disclosed herein can be prepared from by selectively glycosylating an appropriate acceptor with a GlcNHC(O)$R^a$ donor as shown below:

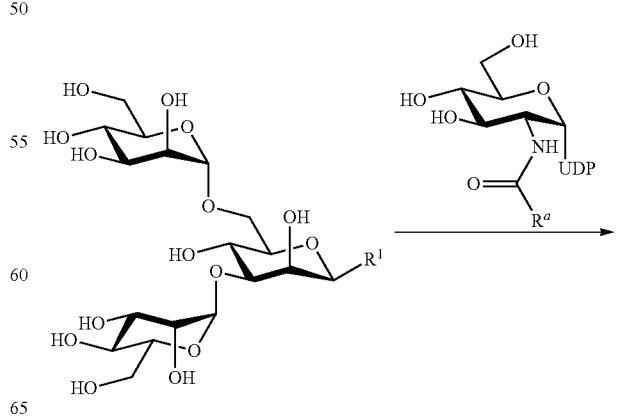

-continued

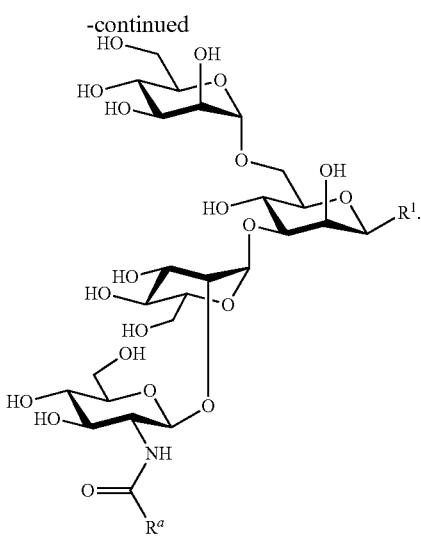

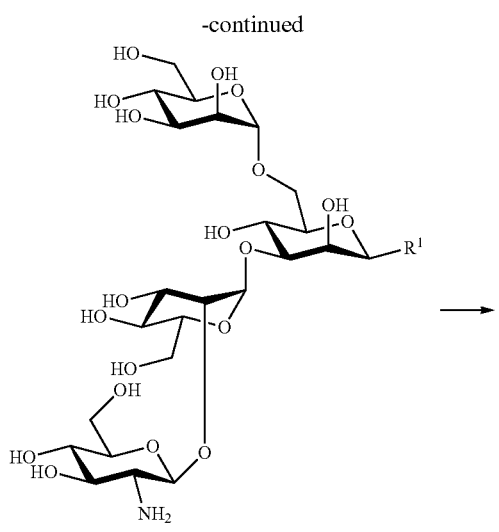

wherein R¹ has the meaning given above, and $R^a$ is $CX_3$, $CHX_2$, $CH_2X$, $CH_3$, OBn, wherein X is in each case independently selected from F, Cl, Br, and I, and UDP is a residue having the formula:

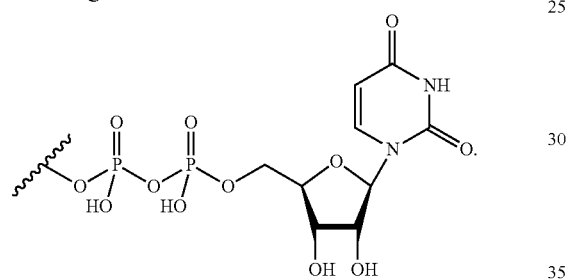

The above glycosylation may be carried out using a suitable glycosyltransferase, for instance α-1,3-mannosyl-glycoprotein 2-β-N-acetylglucosaminyltransferase, referred to herein as MGAT1.

In certain embodiments, when $R^a$ is $CX_3$, $CHX_2$, $CH_2X$, or OBn, the haloacetamide or Cbz group can be removed to furnish the free amine, which can be further elaborated to $R^4$ as defined herein:

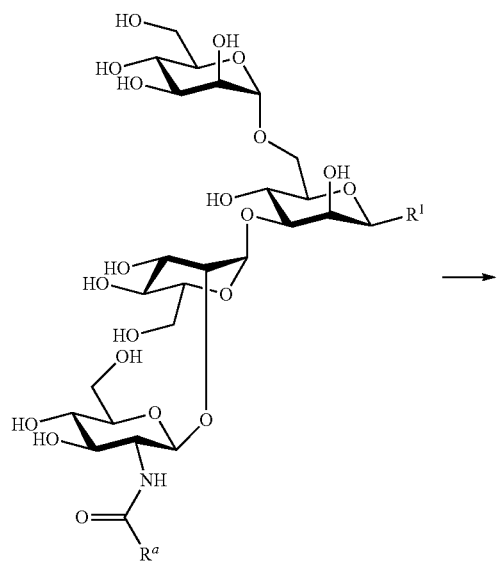

In some embodiments, $R^4$ can be azide. After glycosylation with MGAT1, the resulting product (either with or without conversion to the free amine or the $R^4$ group) can be selectively glycosylated with a further $GlcNHC(O)R^a$ donor:

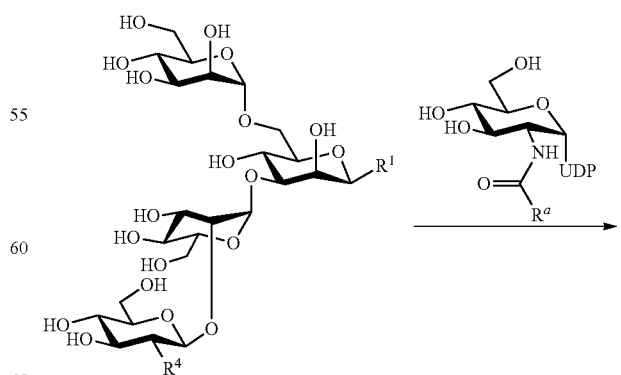

21

-continued

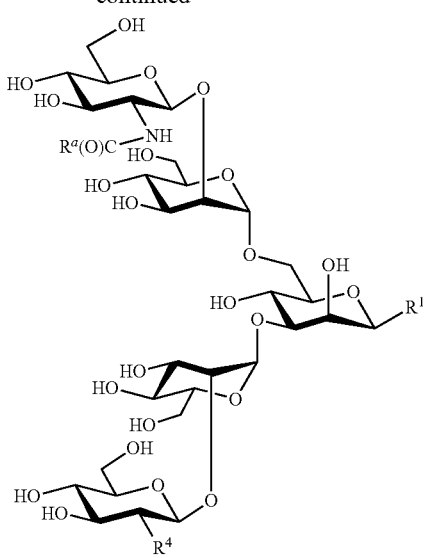

The above glycosylation may be carried out using a suitable glycosyltransferase, for instance α-1,6-mannosyl-glycoprotein 2-β-N-acetylglucosaminyltransferase, referred to herein as MGAT2. In preferred embodiments, $R^4$ and GlcNHC(O)$R^a$ are not the same. The resulting oligosaccharide can be further elaborated as described above:

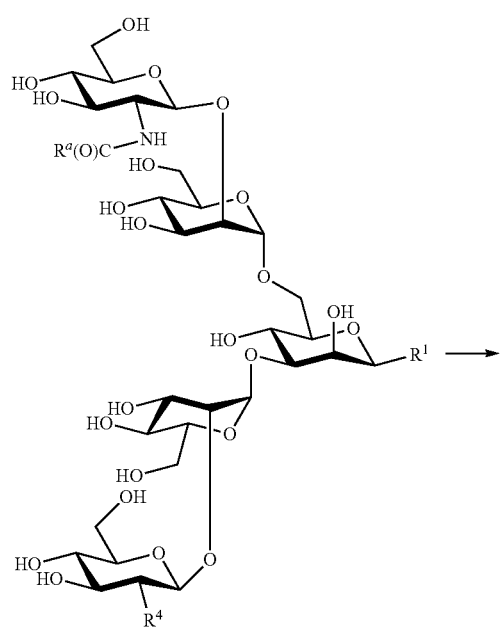

22

-continued

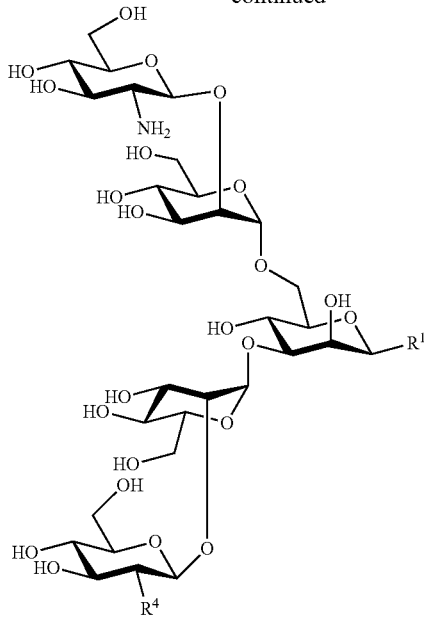

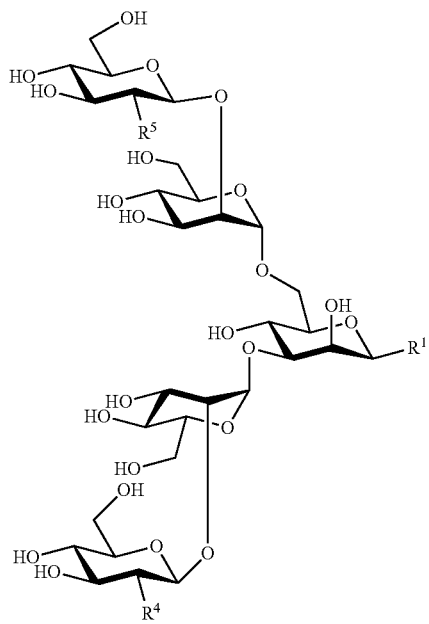

The disclosed compounds are useful intermediates for a variety of additional selective transformations: Use of any of MGAT3, MGAT4, and/or MGAT5 permits selective installation of GlcNHC(O)$R^a$ residues on the oligosaccharide, which can be converted to $R^6$, $R^7$, and $R^8$ residues as defined above.

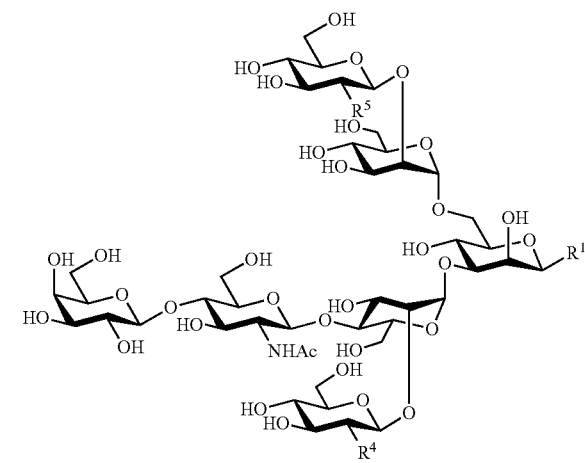

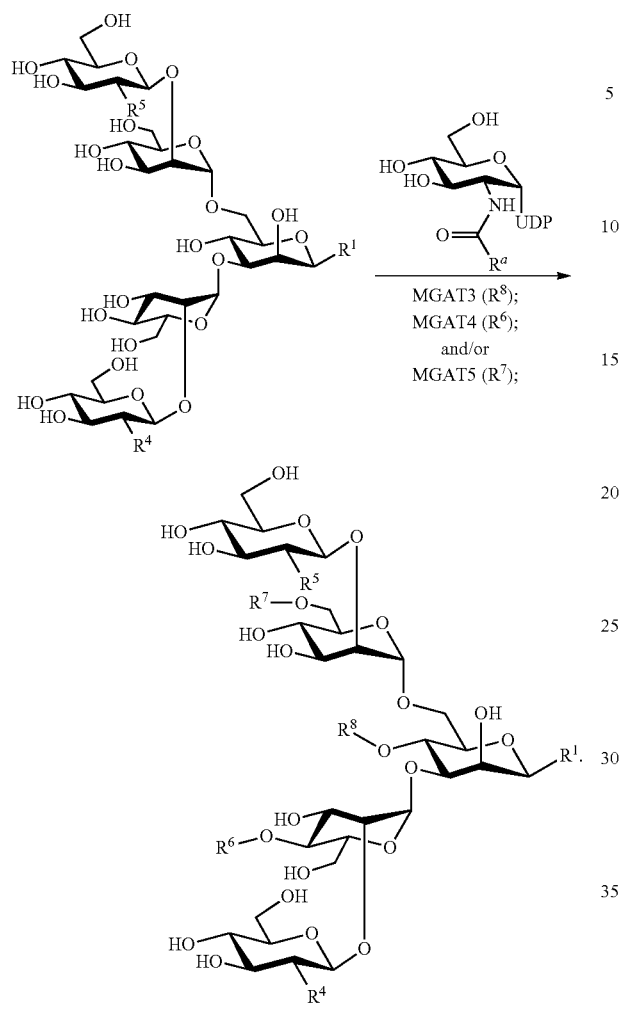

As $R^4$ and $R^5$ can be selected to deactivate those GlcNAc derivatives to galactosyltransferases (e.g., when neither $R^4$ nor $R^5$ are NHC(O)$R^a$, selective elaboration of the oligosaccharide at other arms of the glycan can be achieved:

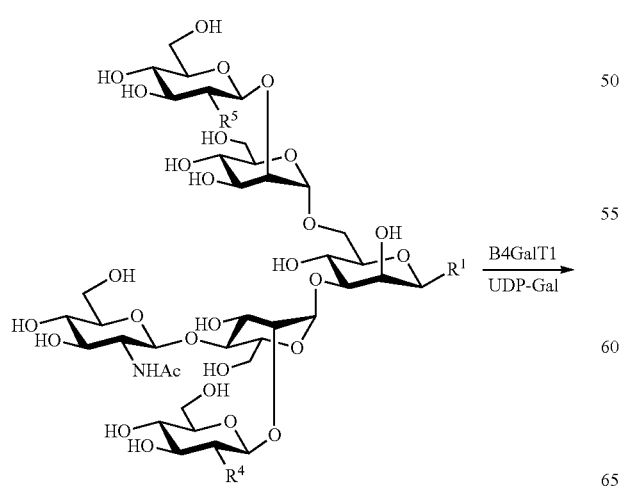

Also disclosed herein are oligosaccharides having the formula:

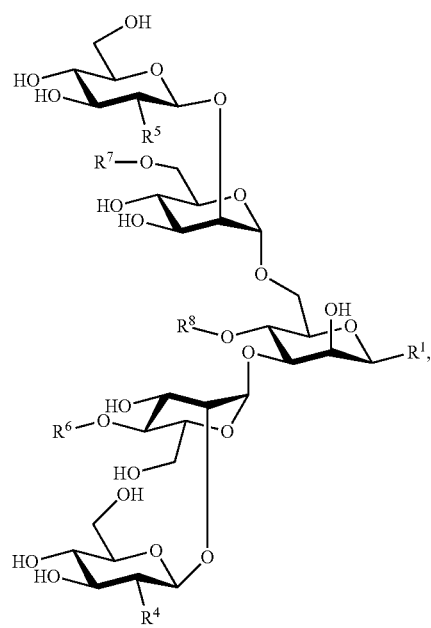

wherein $R^1$, $R^4$, and $R^5$ are as defined above;

$R^6$ can be hydrogen or a residue having the formula:

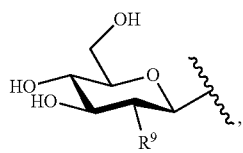

wherein $R^9$ can be $N_3$, $NR^{9a}R^{9b}$, wherein $R^{9a}$ and $R^{9b}$ are the same or different, and can be H, Z—$X^9$ wherein Z can be null, C=O, $SO_2$, and $X^9$ can be $C_{1-4}$alkyl, O—$C_{1-4}$alkyl, $C_{1-4}$haloalkyl, O—$C_{1-4}$haloalkyl, $C_{1-4}$alkylaryl, O—$C_{1-4}$alkylaryl, aryl, O-aryl; or $R^{9a}$ and $R^{9b}$ can together form a ring; or R⁹ can be a radical having the formula:

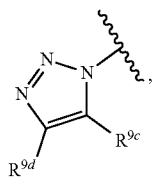

wherein one or both of $R^{9c}$ or $R^{9d}$ constitute a conjugated payload.

In certain embodiments, $R^{9a}$ can be H and $R^{9b}$ can be methoxymethyl, methylthiomethyl, p-methoxybenzyloxymethyl, p-nitrobenzyloxymethyl, t-butoxymethyl, 2-methoxyethoxymethyl, 1-ethoxyethyl, allyl, p-methoxybenzyloxycarbonyl (Moz), p-nitrobenzyloxycarbonyl (PNZ), trimethylsilyl, diethylisopropylsilyl, triphenylsilyl, formyl, chloroacetyl, methanesulfonyl, tosyl, benzylsulfonyl, methoxymethylcarbonyl, benzyloxycarbonyl, carboxybenzyl (Cbz), t-butyloxycarbonyl (BOC), 9-fluorenylmethylcarbonyl, N-phenylcarbamoyl, [2-(trimethylsilyl)ethoxy]methyl, or 4,4'-dimethoxytrityl.

Disclosed herein are compounds listed in the following table:

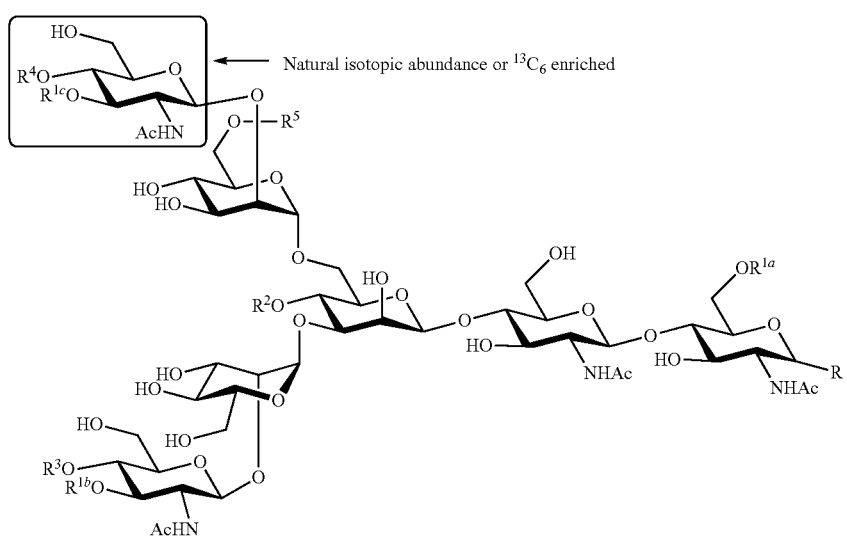

← Natural isotopic abundance or ¹³C₆ enriched

The compounds may be characterized by a natural isotopic abundance for the indicated GlcNAc residue, or that residue may be $^{13}C$-enriched as defined herein.

| Compound 1 | |
|---|---|
| $R^{1a}, R^{1b}, R^{1c}, R^2, R^3, R^4, R^5$ | H |

| Compound 2 | |
|---|---|
| $R^{1b}, R^{1c}, R^2, R^3, R^4, R^5$ | H |
| $R^{1a}$ | 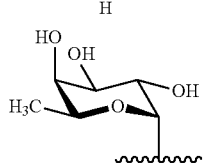 |

| Compound 3 | |
|---|---|
| $R^{1b}, R^{1c}, R^2, R^3, R^5$ | H |
| $R^{1a}$ | 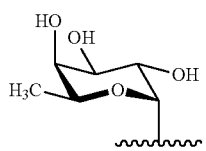 |

| | |
|---|---|
| $R^4$ | 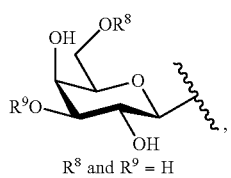$R^8$ and $R^9$ = H |
Compound 4
| | |
|---|---|
| $R^{1a}, R^{1b}, R^{1c}, R^2, R^5$ | H |
| $R^3$ | 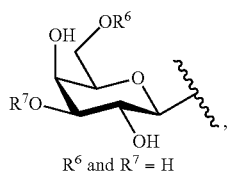$R^6$ and $R^7$ = H |
| $R^4$ | 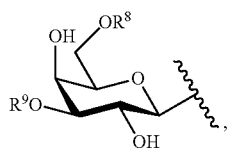 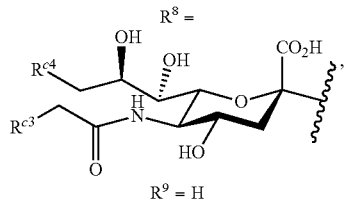$R^9$ = H |
Compound 5
| | |
|---|---|
| $R^{1b}, R^{1c}, R^2, R^5$ | H |
| $R^{1a}$ | 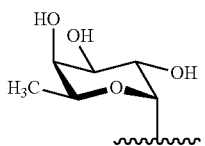 |
| $R^3$ | 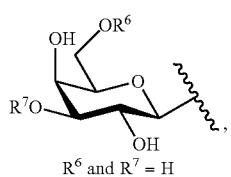$R^6$ and $R^7$ = H |
| $R^4$ | 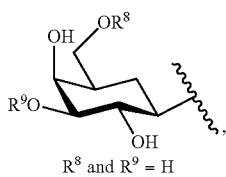$R^8$ and $R^9$ = H |

| Compound 6 | |
|---|---|
| $R^{1a}, R^{1b}, R^{1c}, R^2, R^5$ | H |
| $R^3$ | 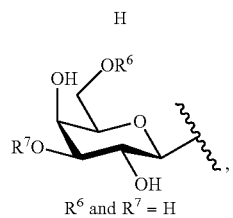<br>$R^6$ and $R^7$ = H |
| $R^4$ | 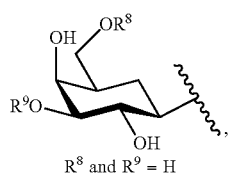<br>$R^8$ and $R^9$ = H |
| Compound 7 | |
| $R^{1a}, R^{1b}, R^{1c}, R^2, R^5$ | H |
| $R^3$ | 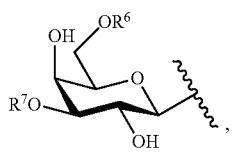 |
| $R^7 =$ | 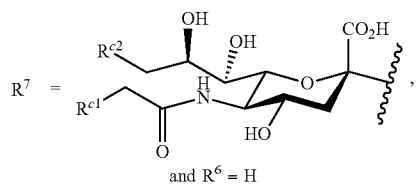<br>and $R^6$ = H |
| $R^4$ | 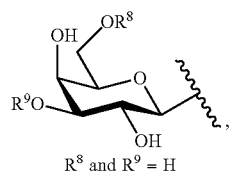<br>$R^8$ and $R^9$ = H |
| Compound 8 | |
| $R^{1a}, R^{1b}, R^{1c}, R^2, R^5$ | H |
| $R^3$ | 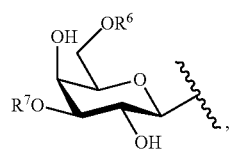 |
| $R^7 =$ | 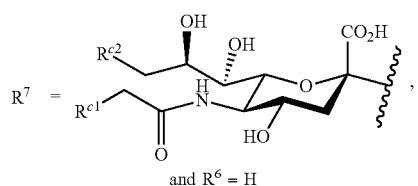<br>and $R^6$ = H |
| $R^4$ | 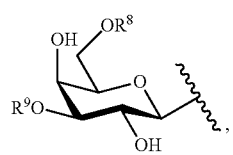 |

| | |
|---|---|
| | $R^9 =$ 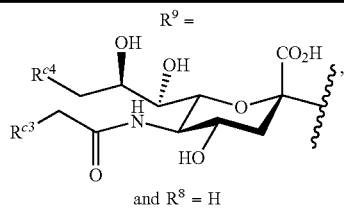, and $R^8 = H$ |
| Compound 9 | |
| $R^{1a}, R^{1b}, R^{1c}, R^2, R^5$ | H |
| $R^3$ | 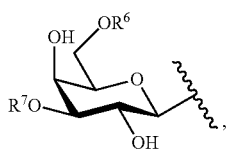, $R^7 =$ 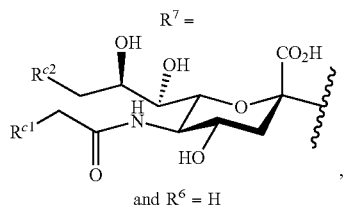, and $R^6 = H$ |
| $R^4$ | 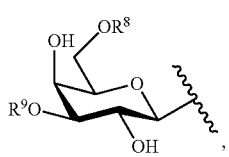, $R^8 =$ 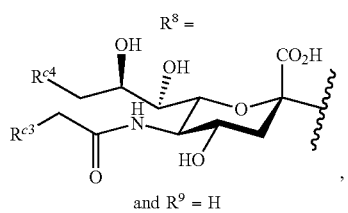, and $R^9 = H$ |
| Compound 10 | |
| $R^{1a}, R^{1b}, R^{1c}, R^2, R^5$ | H |
| $R^3$ | 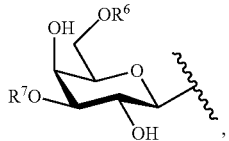, $R^6 =$ 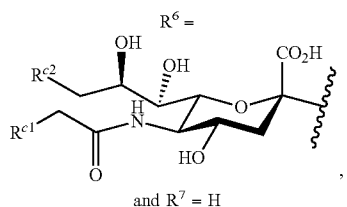, and $R^7 = H$ |
| $R^4$ | 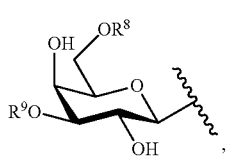, |

-continued
| | | |
|---|---|---|
| | R⁸ = 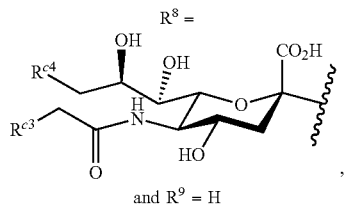 and R⁹ = H | |
Compound 11
| | | |
|---|---|---|
| $R^{1a}, R^{1b}, R^{1c}, R^2, R^5$ | H | |
| $R^3$ | 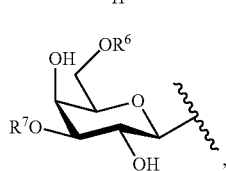 | |
| | R⁶ = 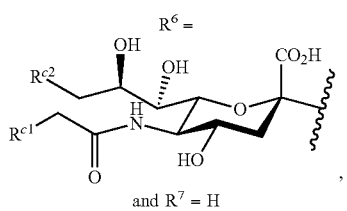 and R⁷ = H | |
| $R^4$ | 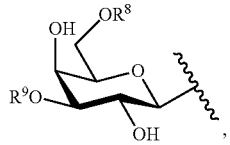 | |
| | R⁹ = 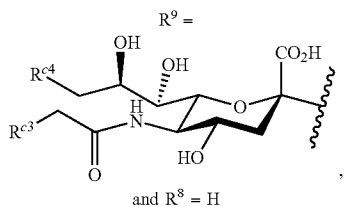 and R⁸ = H | |
Compound 12
| | | |
|---|---|---|
| $R^{1b}, R^{1c}, R^2, R^5$ | H | |
| $R^{1a}$ | 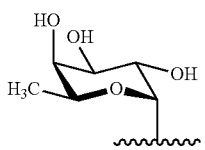 | |
| $R^3$ | 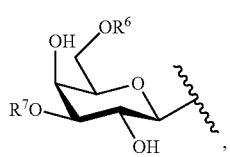 | |
| | R⁷ = 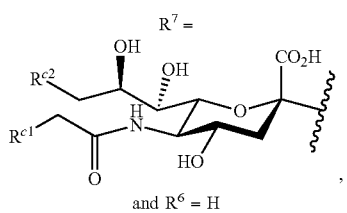 and R⁶ = H | |

-continued
| | |
|---|---|
| $R^4$ | 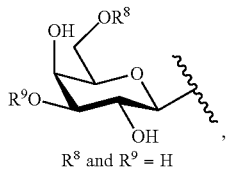, $R^8$ and $R^9$ = H |
Compound 13
| | |
|---|---|
| $R^{1b}, R^{1c}, R^2, R^5$ | H |
| $R^{1a}$ | 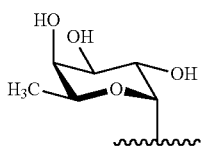 |
| $R^3$ | 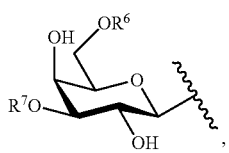, $R^7$ = 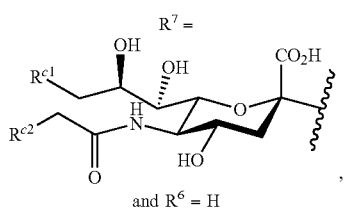, and $R^6$ = H |
| $R^4$ | 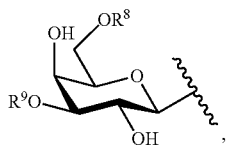, $R^9$ = 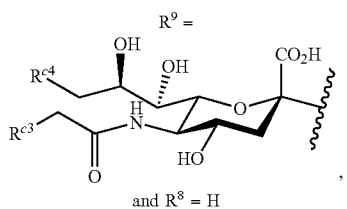, and $R^8$ = H |
Compound 14
| | |
|---|---|
| $R^{1b}, R^{1c}, R^5$ | H |
| $R^{1a}$ | 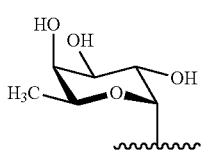 |
| $R^2$ | 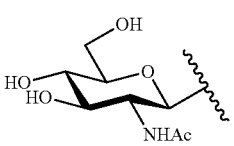 |

| | |
|---|---|
| R³ | 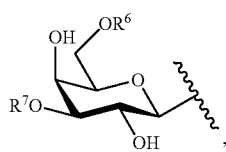 , |
| | R⁶ = 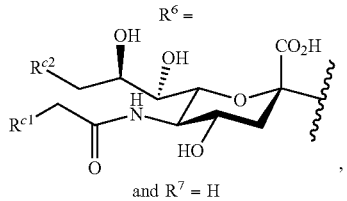 , and R⁷ = H |
| R⁴ | 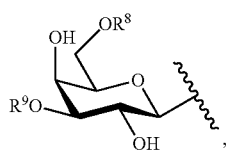 , |
| | R⁹ = 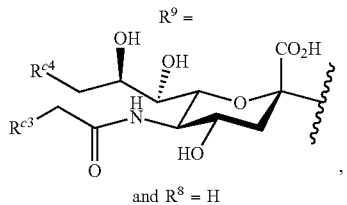 , and R⁸ = H |
| Compound 15 | |
| R¹ᵇ, R¹ᶜ, R⁵ | H |
| R¹ᵃ | 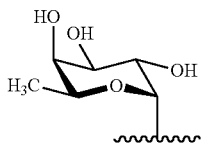 |
| R² | 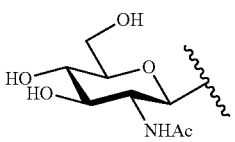 |
| R³ | 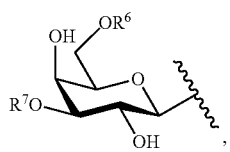 , |
| | R⁶ = 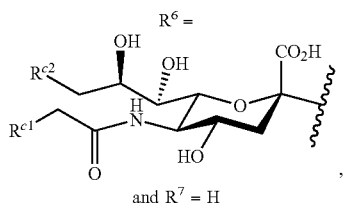 , and R⁷ = H |

-continued
| | |
|---|---|
| R⁴ | 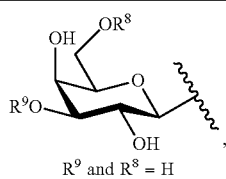  R⁹ and R⁸ = H |
Compound 16
| | |
|---|---|
| R^{1b}, R^{1c}, R⁵ | H |
| R^{1a} | 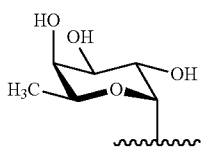 |
| R² | 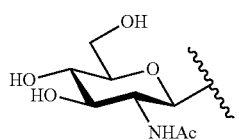 |
| R³ | 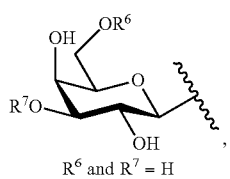  R⁶ and R⁷ = H |
| R⁴ | 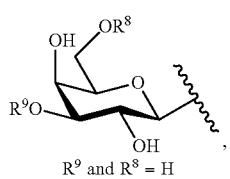  R⁹ and R⁸ = H |
Compound 17
| | |
|---|---|
| R^{1a}, R^{1b}, R^{1c}, R² | H |
| R³ | 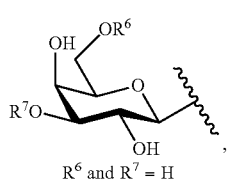  R⁶ and R⁷ = H |
| R⁴ | 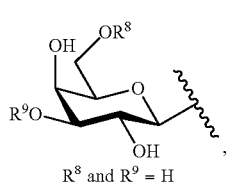  R⁸ and R⁹ = H |
| R⁵ | 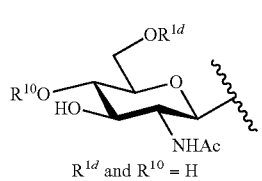  R^{1d} and R^{10} = H |

-continued
| Compound 18 | |
|---|---|
| $R^{1a}, R^{1b}, R^{1c}, R^2$ | H |
| $R^3$ | 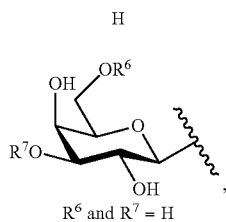 $R^6$ and $R^7$ = H |
| $R^4$ | 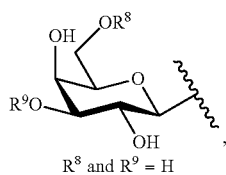 $R^8$ and $R^9$ = H |
| $R^5$ | 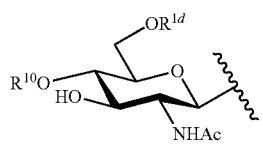 $R^{10}$ = 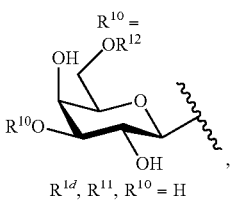 $R^{1d}, R^{11}, R^{10}$ = H |
| Compound 19 | |
|---|---|
| $R^{1a}, R^{1b}, R^{1c}, R^2$ | H |
| $R^3$ | 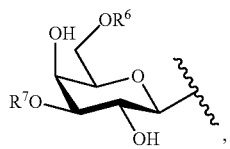 $R^7$ = 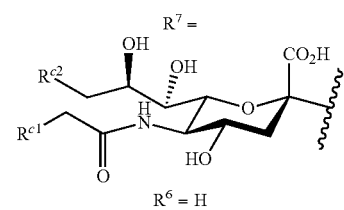 $R^6$ = H |
| $R^4$ | 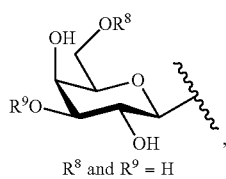 $R^8$ and $R^9$ = H |
| $R^5$ | 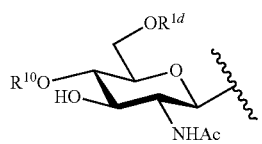 |

-continued
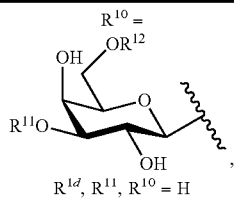
$R^{1d}$, $R^{11}$, $R^{10}$ = H
Compound 20
| $R^{1a}$, $R^{1b}$, $R^{1c}$, $R^2$ | H |
|---|---|
| $R^3$ | 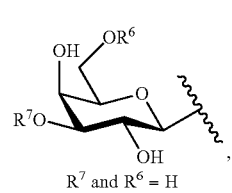 $R^7$ and $R^6$ = H |
| $R^4$ | 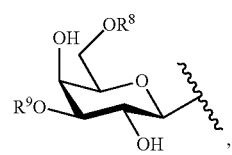 |
$R^9$ =
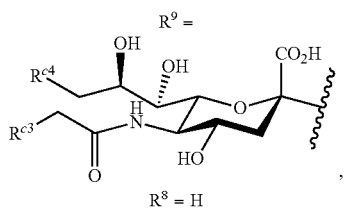
$R^8$ = H
| $R^5$ | 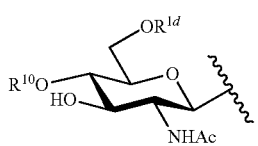 |
|---|---|
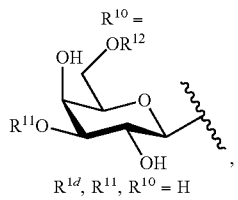
$R^{1d}$, $R^{11}$, $R^{10}$ = H
Compound 21
| $R^{1a}$, $R^{1b}$, $R^{1c}$, $R^2$ | H |
|---|---|
| $R^3$ | 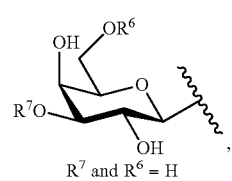 $R^7$ and $R^6$ = H |
| $R^4$ | 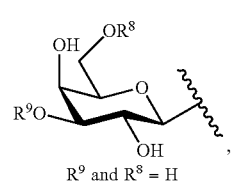 $R^9$ and $R^8$ = H |

-continued
| | |
|---|---|
| R⁵ | 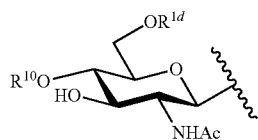, 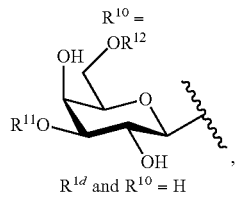, R¹ᵈ and R¹⁰ = H 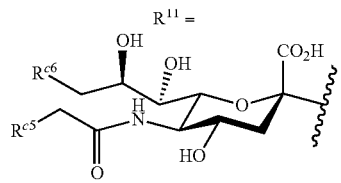 |
Compound 22
| | |
|---|---|
| R¹ᵃ, R¹ᵇ, R¹ᶜ, R² | H |
| R³ | 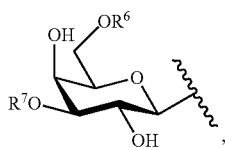, 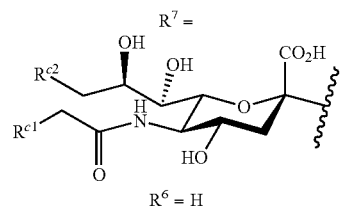 R⁶ = H |
| R⁴ | 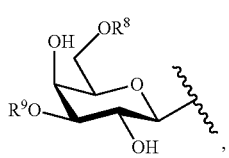, 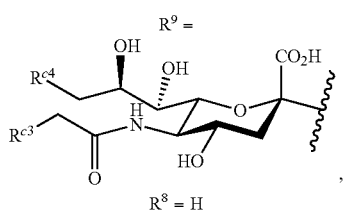, R⁸ = H |
| R⁵ | 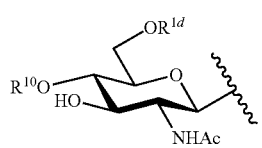 |

-continued
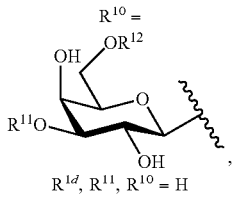
$R^{1d}, R^{11}, R^{10} = H$
Compound 23
| $R^{1a}, R^{1b}, R^{1c}, R^2$ | H |
|---|---|
| $R^3$ | 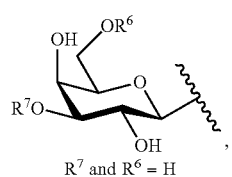 $R^7$ and $R^6 = H$ |
| $R^4$ | 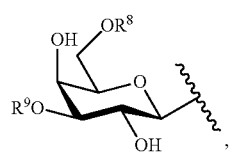 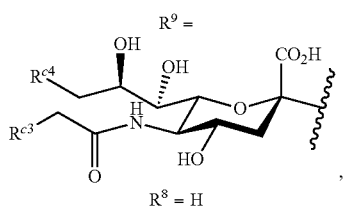 $R^8 = H$ |
| $R^5$ | 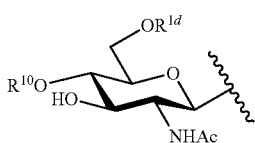 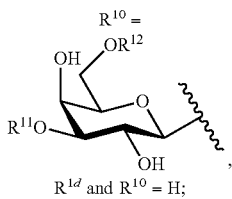 $R^{1d}$ and $R^{10} = H$; |

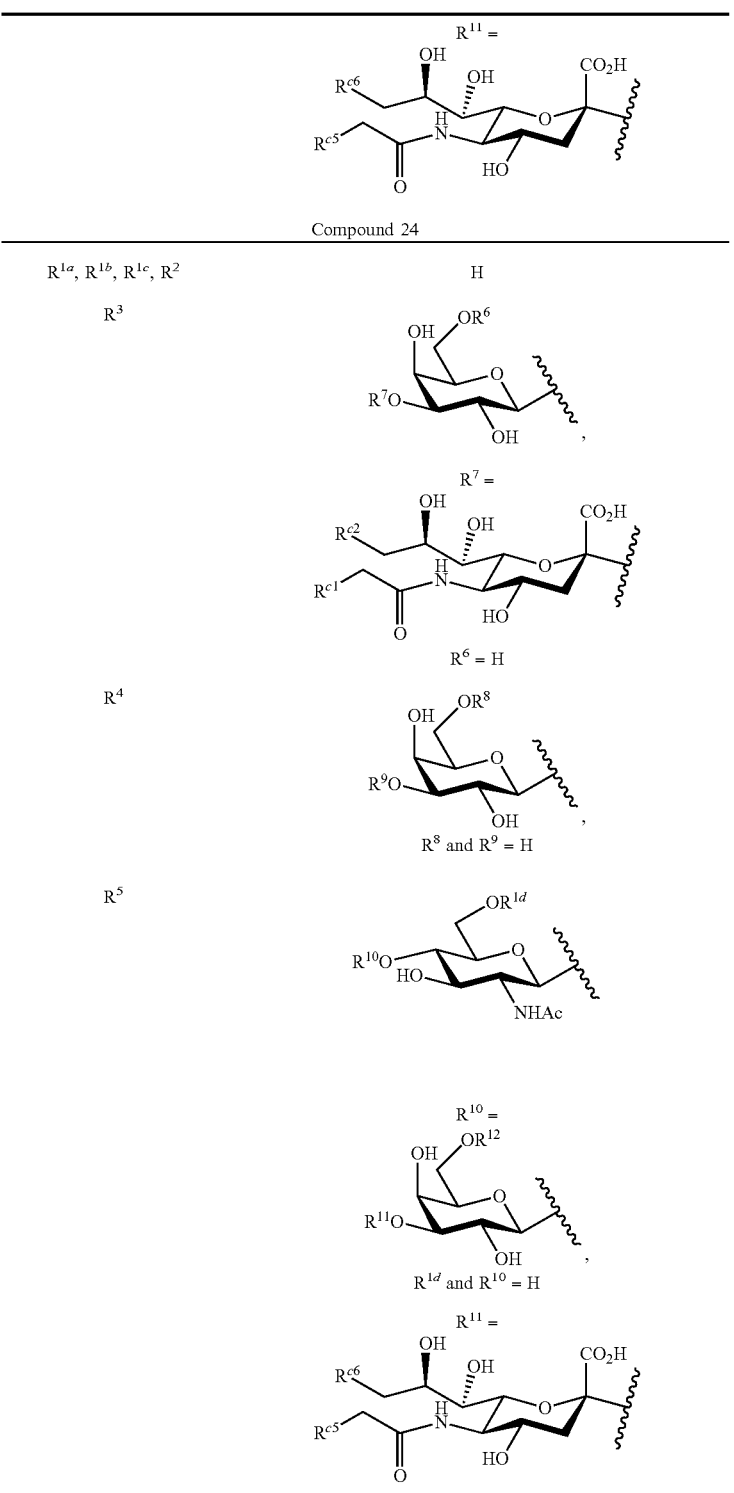

The disclosed compounds are useful as analytical standard for the characterization and quantification of N-glycans. In some embodiments are provided kits containing at least one, isolated compound in a vial. Preferably, the compound will be present in the vial as a lyophilized mixture, optionally in combination with one or more inert bulking or stabilizing agents. The purity of the compound in the vial can be at least 90%, at least 95%, at least 98%, or at least 99%, as measured by HPLC. Some kits may contain multiple vials, each containing a single compound different from the rest. Exemplary kits may include at least 2 compounds, at least 3 compounds, at least 5 compounds, at least 8 compounds, at least 10 compounds, at least 12 compounds, at least 15 compounds, or at least 20 compounds disclosed herein.

Also disclosed are oligosaccharides having the formula:

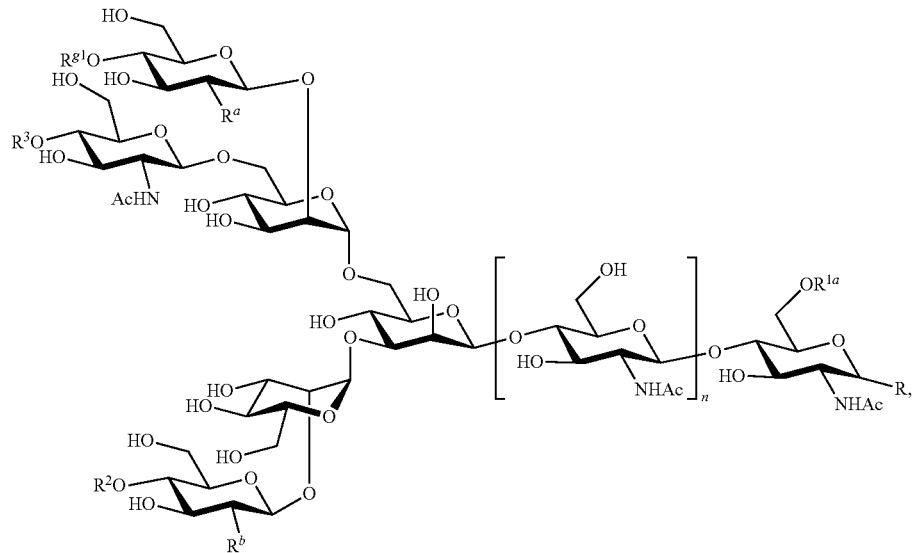

and salts thereof, wherein n is 1 or 0;
$R^a$ is $N_3$, or $NR^{4a}R^{4b}$.
wherein $R^{4a}$ and $R^{4b}$ are independently selected from H or Z—$X^4$,
wherein Z is null, C=O, or $SO_2$, and $X_4$ is $C_{1-4}$alkyl, O—$C_{1-4}$alkyl, $C_{1-4}$haloalkyl, O—$C_{1-4}$haloalkyl, $C_{1-4}$alkylaryl, O—$C_{1-4}$alkylaryl, aryl, or O-aryl; or
$R^{4a}$ and $R^{4b}$ can together form a ring; or
$R^a$ is a radical having the formula:

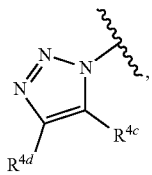

wherein one or both of $R^{4c}$ or $R^{4d}$ constitute a conjugated payload;
$R^b$ is $N_3$, or $NR^{4a}R^{4b}$,
wherein $R^{4a}$ and $R^{4b}$ are independently selected from H or Z—$X^4$,
wherein Z is null, C=O, or $SO_2$, and $X^4$ is $C_{1-4}$alkyl, O—$C_{1-4}$alkyl, $C_{1-4}$haloalkyl, O—$C_{1-4}$haloalkyl, $C_{1-4}$alkylaryl, O—$C_{1-4}$alkylaryl, aryl, or O-aryl; or
$R^{4a}$ and $R^{4b}$ can together form a ring; or $R^b$ is a radical having the formula:

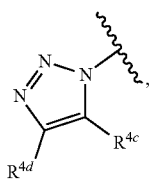

wherein one or both of $R^{4c}$ or $R^{4d}$ constitute a conjugated payload;

provided that $R^a$ and $R^b$ are not both $NHC(O)CH_3$;
$R^{1a}$ is hydrogen or α-(L)-fucose, and
$R^3$, $R^2$, and $R^{g1}$ are independently selected from hydrogen or further carbohydrate, for instance a monosaccharide or oligosaccharide. Exemplary $R^3$, $R^2$, and $R^{g1}$ groups include N-acetylglucosamine (GlcNAc), galactose (Gal), sialic acid (Neu5Ac), and oligosaccharide comprising the same. Exemplary sequences are depicted in Figure In some instances $R^3$ can be a moiety having the formula:

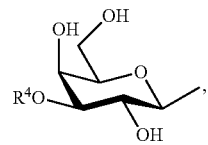

wherein $R^4$ is selected from hydrogen or further carbohydrate, for instance a monosaccharide or oligosaccharide. In some instances $R^4$ can be a moiety having the formula:

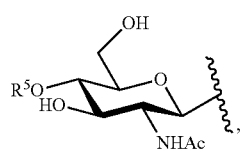

wherein $R^5$ is selected from hydrogen or further carbohydrate, for instance a monosaccharide or oligosaccharide. In some instances $R^5$ can be a moiety having the formula:

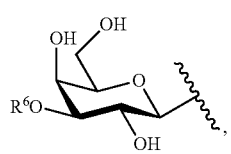

wherein $R^6$ is selected from hydrogen or further carbohydrate, for instance a monosaccharide or oligosaccharide. In some instances $R^6$ can be a moiety having the formula:

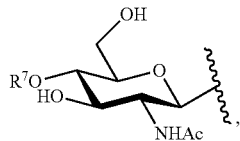

wherein $R^7$ is selected from hydrogen or further carbohydrate, for instance a monosaccharide or oligosaccharide. In some instances $R^7$ can be a moiety having the formula:

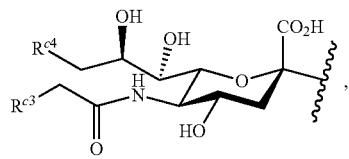

wherein $R^{c3}$ is selected from hydrogen or conjugated payload, and $R^{c4}$ is selected from OH or conjugated payload.

In some instances $R^2$ can be a moiety having the formula:

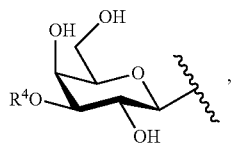

wherein $R^4$ is hydrogen or further carbohydrate, for instance a monosaccharide or oligosaccharide. In some instances $R^4$ can be a moiety having the formula:

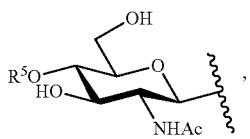

wherein $R^5$ is hydrogen or further carbohydrate, for instance a monosaccharide or oligosaccharide. In some instances $R^5$ can be a moiety having the formula:

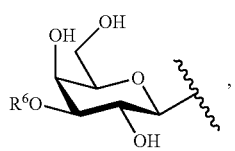

wherein $R^6$ is hydrogen or further carbohydrate, for instance a monosaccharide or oligosaccharide. In some instances $R^6$ can be a moiety having the formula:

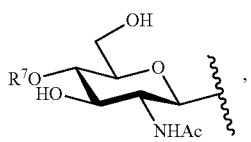

wherein $R^7$ is hydrogen or further carbohydrate, for instance a monosaccharide or oligosaccharide. In some instances $R^7$ can be a moiety having the formula:

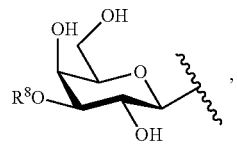

wherein $R^8$ is hydrogen or a carbohydrate moiety having the formula:

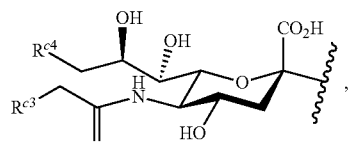

wherein $R^{c3}$ is selected from hydrogen or conjugated payload, and $R^{c4}$ is selected from OH or conjugated payload.

$R^{g1}$ is hydrogen or a carbohydrate moiety having the formula:

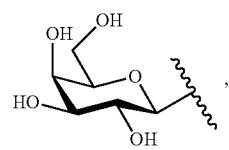

$R^2$ is hydrogen or a carbohydrate moiety having the formula:

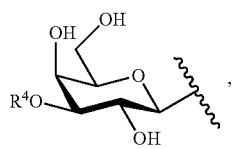

wherein $R^4$ is hydrogen or a carbohydrate moiety having the formula:

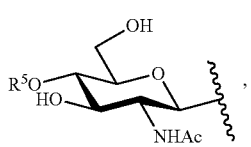

wherein $R^5$ is hydrogen or a carbohydrate moiety having the formula:

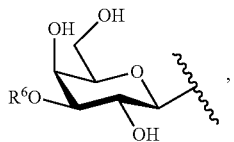

wherein R[6] is hydrogen or a carbohydrate moiety having the formula:

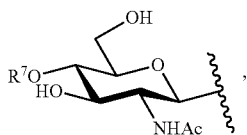

wherein R[7] is hydrogen or a carbohydrate moiety having the formula:

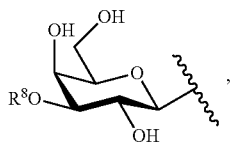

wherein R[8] is hydrogen or a carbohydrate moiety having the formula:

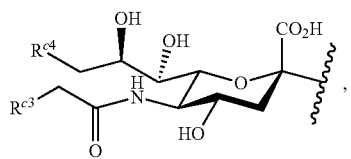

wherein R[c3] is selected from hydrogen or conjugated payload, and R[c4] is selected from OH or conjugated payload.

EXAMPLES

The following examples are for the purpose of illustration of the invention only and are not intended to limit the scope of the present invention in any manner whatsoever.

[1]H spectra were recorded on a 600 MHZ Varian Inova or an Agilent 900 MHZ DD2 spectrometer with a triple resonance (HCN) cryogenically cooled probe spectrometer. Chemical shifts are reported in parts per million (ppm) relative to H1 and C1 of reducing N-acetylglucosamine which were set to δ 5.08 and 78.02 respectively as the internal standard. NMR data is represented as follows: Chemical shift, multiplicity (s=singlet, d=doublet, t=triplet, dd=doublet of doublets, m=multiplet and/or multiple resonances, br.=broad signal), J coupling, integration, and peak identity. NMR signals were assigned based on $^1$H NMR, gCOSY, gHSQC, zTOCSY, and NOESY experiments. Enzymatic reactions were monitored by mass spectrometry recorded on an Applied Biosystems SCIEX MALDI TOF/TOF 5800 using 2,5-dihydroxybenzoic acid (DHB) as a matrix or a Shimadzu 20AD UFLC LCMS-IT-TOF. Reagents were purchased from Sigma-Aldrich (unless otherwise noted) and used without further purification. HILIC-HPLC purification of compounds was performed on a Shimadzu 20AD UFLC LCMS-IT-TOF with a Waters XBridge BEH, Amide column, 5 μm, 10×250 mm. HPLC grade acetonitrile and water were purchased from Fischer. Uridine 5'-diphosphogalactose diphosphate galactose (UDP-Gal) and cytidine-5'monophospho-N-acetylneuraminc acid (CMP-Neu5Ac) were both purchased from Roche, uridine 5'-diphospho-N-acetylglucosamine (UDP-GlcNAc) was purchased from Sigma-Aldrich, and guanosine 5'-diphospho-β-L-fucose (GDP-Fuc) was purchased from Carbosynth.

2b. Extraction, Isolation and Trimming of SGP

Sialyl Glycopeptide (SGP, 5) Extraction

SGP (5) was extracted according to our previously reported procedure[1]. In short, commercially available egg yolk powder (Natural Foods, Inc., 2.27 Kg) was suspended twice in 95% ethanol (4 L) and mechanically stirred for 2 h at room temperature to remove lipids and other organic soluble components. The filtrate was discarded and the insoluble powder was suspended twice in aqueous ethanol (40% w/v ethanol, 3 L) solution. The insoluble material was discarded and the filtrate was concentrated under reduced pressure at 40° C. The resulting translucent liquid was purified using an active carbon/celite column (500 g of active carbon and 500 g celite). Impurities were removed by flushing the column with 3 L of water (0.1% v/v TFA), 3 L of 5% acetonitrile in water (0.1% v/v TFA), and 3 L 10% acetonitrile in water (0.1% v/v TFA). The desired glycopeptide was released from the column using a solution of 25% acetonitrile in water (0.1% v/v TFA), and fractions containing the product were pooled and dried under reduced pressure. The resulting white powder was subjected to size-exclusion chromatography (Bio-Rad® P-2, fine particle size 45-90 μm, column dimensions 5.0 cm×80 cm, 250 mL fractions) eluting with 0.1 M ammonium bicarbonate to yield SGP (5) as a fluffy, white powder (1.82 g, or 0.8 mg SGP/g egg yolk powder).

Trimming and Modification of SGP to Prepare Glycosyl Asparagine-CBz 1[1] Isolated SGP 5 (319 mg) was dissolved in 5 mL of Tris buffer (100 mM, pH 8.0) containing 5 mM CaCl$_2$. Pronase from *Streptomyces griseus* (Sigma-Aldrich #P5147-1G, 150 mg) was added, and the reaction was incubated for 5 days at 37° C. with shaking. The reaction was monitored by ESI-MS and once complete the mixture was heated at 80° C. for 20 min followed by Pronase removal using an Amicon Ultra-10 (MWCO-10k) centrifugal filter. The filtrate was lyophilized and purified by size-exclusion chromatography (Bio-Rad P-2 BioGel, fine particle size 45-90 μm, 2×80 cm), eluting with a 0.1 M ammonium bicarbonate solution. The fractions containing the glycosylated asparagine were pooled, lyophilized, and dissolved in 5 mL of water. To this mixture was added K$_2$CO$_3$ (1.1 g), and CBzCl (0.54 g, 3.2 mmol) drop-wise. The heterogeneous mixture was stirred vigorously at room temperature until ESI-MS indicated complete installation of the CBz-protecting group (6). The reaction was diluted with water (50 mL) and extracted with ethyl acetate (2×50 mL). The organic phase was discarded, and the aqueous phase was lyophilized and purified by size-exclusion chromatography using P-2 BioGel eluting with a 0.1 M ammonium bicarbonate solution. The fractions containing 6 were pooled, lyophilized, and re-dissolved in 5 mL of sodium acetate buffer (50 mM, pH 5.5) containing 5 mM CaCl$_2$. To this mixture was added neuraminidase from *Clostridium perfringens* (New England Biolabs #P0720L, 40 μL, 2000 units) and the reaction was incubated overnight at 37° C. with shaking at which time, ESI-MS indicated all the sialic acid residues had been removed. The pH of the reaction mixture was adjusted to 4.5 with acetic acid after which. BSA (5 mg) and β-galactosidase (200 µL, 800 units) from *Aspergillus niger* (Megazyme #E-BGLAN) were added. The reaction was incubated at 37° C. with shaking overnight, after which another 150 µL of β-galactosidase were added. The reaction was monitored by ESI-MS and once complete galactose removal was observed the enzymes were removed using an Amicon Ultra-10 (MWCO-10k) centrifugal filter. The filtrate was lyophilized and purified by size-exclusion chromatography using P-2 BioGel eluting with a 0.1 M ammonium bicarbonate solution. The fractions containing the trimmed glycosyl asparagine-CBz were pooled, lyophilized, and dissolved in 10 mL of MES buffer (100 mM, pH 7.3). To this mixture BSA (1 mg), calf intestine alkaline phosphatase (CIAP. 100 µL, 2 kU/mL), GDP-Fucose (75 mg), and FUT8 (200 µL, 1 mg/mL) were added and the reaction was incubated overnight at 37° C. with shaking. The reaction was lyophilized and purified by size-exclusion chromatography using P-2 BioGel eluting with a 0.1 M ammonium bicarbonate solution. The fractions containing 1 were pooled, lyophilized, and subjected to HILIC-HPLC (see section 2f) for final purification to give the compound 1 (74 mg, 39%).

2c. Expression and Purification of Enzymes
Recombinant Expression and Purification of PmGlmU The gene sequence of *Pasteurella multocida* N-acetylglucosamine-1-phosphate uridylyltransferase (PmGlmU) from *Pasteurella multocida* strain P-1059 (ATCC 15742) with a C-terminal $His_6$-tag[2] were synthesized, ligated into a pET15b plasmid using NdeI and RhoI restriction sites, and transformed into *E. coli* BL21 (DE3) cells by Genscript. *E. coli* BL21 cells harboring the pET15b-PmGlmU plasmid were cultured in LB medium containing ampicillin (100 µg/mL) at 37° C. until an $OD_{600nm}$ of 0.8-1.0 was reached. Protein expression was induced by the addition of isopropyl-1-thio-β-D-galactopyranoside (IPTG, final concentration 100 M) and cultures where incubated at 20° C. with rigorous shaking for 18 h. The cells were harvested by centrifugation (4,000×g) at 4° C. for 20 min and the resulting pellet was resuspended in lysis buffer (100 mM Tris-HCl, pH=8, containing 0.1% Triton X-100, lysozyme (100 µg/mL) and DNAse (5 µg/mL)). The cells were lysed by passing the suspension twice through a French Press at 10000 PSI and 4° C. and the lysate was clarified by centrifugation (10,000× g) at 4° C. for 45 min. Purification was performed by loading the supernatant onto a Ni-NTA superflow column pre-equilibrated with binding buffer (10 mM imidazole, 0.5 M NaCl, 50 mM Tris-HCl, pH=7.5). The column was washed with washing buffer (40 mM imidazole, 0.5 M NaCl, 50 mM Tris-HCl, pH=7.5) and the PmGlmU enzyme was eluted with elution buffer (200 mM imidazole, 0.5 M NaCl, 50 mM Tris-HCl, pH=7.5). Fractions containing purified PmGlmU enzyme were combined and 10% glycerol was added for storage at 4° C. From 1 L of culture medium 120-150 mg of PmGlmU was obtained.

Human Glycosyl Transferase Expression and Purification

The catalytic domains of human glycosyl transferases (as shown in the table below) were expressed as soluble, secreted fusion proteins by transient transfection of HEK293 suspension cultures[3,4]. The coding regions were amplified from Mammalian Gene Collection clones, human tissue cDNAs, or generated by gene synthesis by a process that appended a tobacco etch virus (TEV) protease cleavage site[5] to the $NH_2$-terminal end of the coding region and attL1 and attL2 Gateway adaptor sites were extended on the 5' and 3' terminal ends of the coding region during transfer to pDONR221 vector backbone[4]. The pDONR221 clones were then recombined via LR clonase reaction into a custom Gateway adapted version of the pGEn2 mammalian expression vector[4] to assemble a recombinant coding region comprised of a 25 amino acid $NH_2$-terminal signal sequence from the *T. cruzi* lysosomal α-mannosidase[6] followed by an 8×His tag, 17 amino acid AviTag,[7] "superfolder" GFP[8], the nine amino acid sequence encoded by attB1 recombination site, followed by the TEV protease cleavage site and the respective glycosyltransferase catalytic domain coding region.

Suspension culture HEK293 cells (Freestyle 293-F cells, Life Technologies, Grand Island, NY) were transfected as previously described[3,4] and the culture supernatant was subjected to $Ni^{2+}$-NTA superflow chromatography (Qiagen, Valencia, CA). Enzyme preparations were eluted with 300 mM imidazole, concentrated by ultrafiltration, and subjected to gel filtration on a Superdex 75 column (GE Healthcare) preconditioned with a buffer containing 20 mM HEPES, pH 7.0, 100 mM NaCl, 10% glycerol, 0.05% Na azide. Peak fractions were pooled and concentrated to ~1 mg/mL using an ultrafiltration pressure cell membrane (Millipore, Billerica, MA) with a 10 kDa molecular weight cutoff.

2d. UDP-GlcNTFA Preparation
Procedure for the One-Pot Three-Enzyme Preparation of UDP-GlcNTFA (4)

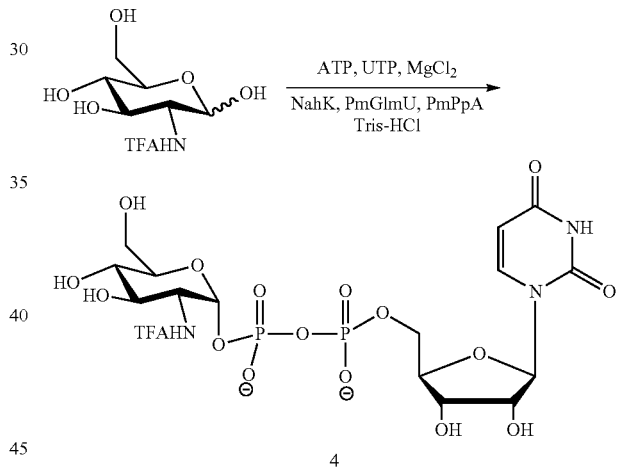

GlcNTFA® (162 mg, 589 µmol), ATP (390 mg, 707 µmol) and UTP (390 mg, 707 µmol) were dissolved in 59 mL of 100 mM Tris-HCl buffer (pH=8.0) containing 10 mM $MgCl_2$. To this solution was added *Bifidobacterium longum* N-acetylhexosamine 1-kinase (NahK, 14 µg/µmol substrate), *Pasteurella multocida* N-acetylglucosamine-1-phosphate uridylyltransferase (PmGlmU. 17 µg/µmol substrate) and *Pasteurella multocida* inorganic pyrophosphatase (PmPpA, 7 µg/µmol substrate), and the reaction mixture was incubated overnight at 37° C. with gentle shaking. Reaction progress was monitored by ESI-TOF MS, and once complete 59 mL of cold ethanol was added and the mixture was incubated at 4° C. for 1 h. The reaction mixture was centrifuged and the supernatant was removed, concentrated, and purified by a P2 BioGel column using 0.1 M $NH_4HCO_3$ as eluent, followed by silica gel column chromatography (4:2:1 EtOAc/MeOH/$H_2O$) afforded UDP-GlcNTFA 4 (273 mg, 70%) as a white solid[2]. $^1H$ NMR (500 MHz, $D_2O$): δ 7.97 (d, J=8.1 Hz, 1H, H6-Uridine), 5.99 (d, J=4.5 Hz, 1H, H1-Ribose), 5.98 (d, J=8.0 Hz, 1H, H5-Uridine), 5.63 (dd, J=7.0, 3.3 Hz, 1H, H1-GlcNTFA), 4.42-4.34 (m, 2H, H2-Ribose, H3-Ribose), 4.33-4.28 (m, 1H, H4-Ribose), 4.24 (dd, J=4.5, 2.7 Hz, 1H, H5-Ribose). 4.21 (dd, J=5.6, 3.0 Hz, 1H, H5'-Ribose), 4.12 (dt, J=10.8, 2.9 Hz, 1H, H2-GlcNTFA), 4.00-3.95 (m, 2H. H3-GlcNTFA. H4-GlcNTFA), 3.89 (dd, J=12.5, 2.3 Hz, 1H, H6-GlcNTFA), 3.83 (dd, J=12.6, 4.3 Hz, 1H, H6'-GlcNTFA), 3.62-3.59 (m, 1H, H5-GlcNTFA. $^{13}$C NMR (76 MHz, D$_2$O): δ 141.6 (C6-Uridine), 102.5 (C5-Uridine), 93.7 (C1-GlcNTFA), 88.5 (C1-Ribose), 83.0 (C4-Ribose), 73.7 (C2-Ribose), 73.0 (C3-GlcNTFA), 70.1 (C4-GlcNTFA), 69.5 (C3-Ribose), 69.4 (C5-GlcNTFA), 64.9 (C5-Ribose), 60.1 (C6-GlcNTFA), 54.3 (C2-GlcNTFA). ESI-MS m/z calcd for $C_{17}H_{23}F_3N_3O_{17}P_2$. [M-H]$^-$: 660.0460, found 660.0417.

2e. General Protocols for Enzymatic Reactions and Glycosyl Asparagine Modification General procedure for the installation of core a 1,6 Fuc using FUT8. Glycosyl asparagine acceptor A2-Asn-Cbz (79 mg, 55 μmol) and GDP-Fuc (75 mg, 111.8 μmol) were dissolved at a final acceptor concentration of 10 mM in a MES buffered solution (100 mM, pH 7.5) containing BSA (1% total volume, stock solution=10 mg mL$^{-1}$). Calf intestine alkaline phosphatase (CIAP, 1% total volume, stock solution=1 kU mL$^{-1}$) and FUT8 (40 μg/μmol acceptor) were added, and the reaction mixture was incubated overnight at 37° C. with gentle shaking. Reaction progress was monitored by ESI-TOF MS and if starting material remained after 18 h another portion of FUT8 was added until no starting material could be detected. The reaction mixture was centrifuged over a Nanosep® Omega ultrafiltration device (10 kDa MWCO) to remove reaction proteins and the filtrate was lyophilized. Purification by HPLC using a HILIC column (supporting information 2f) provided desired product as a white fluffy solid (74 mg, 85%).

General Procedure for the Installation of β1,3 GlcNAc Using B3GNT2

Glycosyl asparagine acceptor (1 eq) and UDP-GlcNAc (1.5 eq) were dissolved to provide a final acceptor concentration of 2-5 mM in a HEPES buffered solution (50 mM, pH 7.3) containing KCl (25 mM), MgCl$_2$ (2 mM) and DTT (1 mM). Calf intestine alkaline phosphotase (CIAP, 1% total volume. 1 kU mL$^{-1}$) and B3GNT2 (1% wt/wt relative to acceptor substrate) were added, and the reaction mixture was incubated overnight at 37° C. with gentle shaking. Reaction progress was monitored by MALDI-TOF MS or ESI-TOF MS, and if starting material remained after 18 h another portion of B3GNT2 was added until no starting material could be detected. The reaction mixture was centrifuged over a Nanosep® Omega ultrafiltration device (10 kDa MWCO) to remove reaction proteins and the filtrate was lyophilized. Purification by HILIC HPLC (see section 2f) or P2 size-exclusion column chromatography provided the desired product.

General Procedure for the Installation of β1,2-GlcNTFA Using MGAT1. Glycosyl asparagine acceptor Man3-Asn-Cbz (5.0 mg, 4.3 μmol) and UDP-GlcNTFA (5.7 mg, 8.6 μmol) were dissolved at a final acceptor concentration of 10 mM in a MES buffered solution (100 mM, pH 6.5) containing MnCl$_2$ (10 mM) and BSA (1% total volume, stock solution=10 mg mL$^{-1}$). Calf intestine alkaline phosphatase (CIAP, 1% total volume) and MGAT1 (40 μg/μmol acceptor) were added, and the reaction mixture was incubated overnight at 37° C. with gentle shaking. Reaction progress was monitored by ESI-TOF MS and if starting material remained after 18 h another portion of MGAT1 was added until no starting material could be detected. The reaction mixture was centrifuged over a Nanosep® Omega ultrafiltration device (10 kDa MWCO) to remove reaction proteins and the filtrate was lyophilized. Purification by HPLC using a HILIC column provided desired product as a white fluffy solid (4.9 mg, 81%).

General Procedure for the Installation of β1,2-GlcNTFA using MGAT2. Glycosyl asparagine acceptor Man3A1-Asn-Cbz (3.0 mg, 2.2 μmol) and UDP-GlcNTFA (3 mg, 4.5 μmol) were dissolved at a final acceptor concentration of 5 mM in a MES buffered solution (100 mM, pH 7.5) containing BSA (1% total volume). CIAP (1% total volume) and MGAT2 (400 μg/μmol acceptor) were added, and the reaction mixture was incubated overnight at 37° C. with gentle shaking. Reaction progress was monitored by ESI-TOF MS, and if starting material remained after 18 h another portion of MGAT2 was added until no starting material could be detected. The reaction mixture was centrifuged over a Nanosep® Omega ultrafiltration device (10 kDa MWCO) to remove reaction proteins, and the filtrate was lyophilized. Purification by HPLC using a HILIC column provided the desired product Man3A2-Asn-Cbz as a white fluffy solid (2.7 mg, 76%).

General Procedure for the Installation of β1,6-GlcNTFA Using MGAT5. Glycosyl asparagine acceptor 1 (17.6 mg, 10.2 μmol) and UDP-GlcNTFA (13.5 mg, 20.4 μmol) were dissolved at a final acceptor concentration of 10 mM in a sodium cacodylate buffered solution (100 mM, pH 6.5) containing MnCl$_2$ (10 mM) and BSA (1% total volume, stock solution=10 mg mL$^{-1}$). Calf intestine alkaline phosphatase (CIAP, 1% total volume, stock solution=1 kU mL$^{-1}$) and MGAT5 (40 μg/μmol acceptor) were added, and the reaction mixture was incubated overnight at 37° C. with gentle shaking. Reaction progress was monitored by MALDI-TOF MS and if starting material remained after 18 h another portion of MGAT5 was added until no starting material could be detected. The reaction mixture was centrifuged over a Nanosep® Omega ultrafiltration device (10 kDa MWCO) to remove reaction proteins and the filtrate was lyophilized. Purification by HPLC using a HILIC column (supporting information 2f) provided desired product 14 as a white fluffy solid (18.6 mg, 92%).

General Procedure for the Installation of β1,4-GlcNTFA Using MGAT4B. Glycosyl asparagine acceptor 2 (4.0 mg, 2.1 μmol) and UDP-GlcNTFA (2.75 mg, 4.2 μmol) were dissolved at a final acceptor concentration of 5 mM in a Tris buffered solution (100 mM, pH 7.5) containing MnCl$_2$ (5 mM) and BSA (1% total volume). CIAP (1% total volume) and MGAT4B (400 μg/μmol acceptor) were added, and the reaction mixture was incubated overnight at 37° C. with gentle shaking. Reaction progress was monitored by ESI-TOF MS, and if starting material remained after 18 h another portion of MGAT4B was added until no starting material could be detected. The reaction mixture was centrifuged over a Nanosep® Omega ultrafiltration device (10 kDa MWCO) to remove reaction proteins, and the filtrate was lyophilized. Purification by HPLC using a HILIC column (supporting information 2f) provided the desired product S6 as a white fluffy solid (3.8 mg, 85%).

General Procedure for the Installation of β1,4 Gal Using B4GALT1

Glycosyl asparagine acceptor (1 eq) and UDP-Gal (1.5 eq per Gal to be added) were dissolved to a provide an acceptor concentration of 2-5 mM in a Tris buffered solution (100 mM, pH 7.5) containing MnCl$_2$ (10 mM) and BSA (1% total volume). CIAP (1% volume total) and B4GALT1 (1% wt/wt relative to acceptor substrate) were added, and the reaction mixture was incubated overnight at 37° C. with gentle shaking. Reaction progress was monitored by MALDI-TOF MS or ESI-TOF MS, and if starting material remained after 18 h another portion of B4GALT1 was added until no starting material could be detected. The reaction mixture was centrifuged over a Nanosep® Omega ultrafiltration device (10 kDa MWCO) to remove reaction proteins and the filtrate was lyophilized. Purification by HILIC HPLC (see section 2f) or P2 size-exclusion column chromatography provided the desired product.

General Procedure for the Installation of α1,3 Fuc Using FUT5

Glycosyl asparagine acceptor (1 eq) and GDP-Fuc (1.5 eq per Fuc to be added) were dissolved at a final acceptor concentration of 2-5 mM in a Tris buffered solution (50 mM, pH 7.3) containing $MnCl_2$ (10 mM). CIAP (1% total volume) and FUT5 (1% wt/wt) were added, and the reaction mixture was incubated overnight at 37° C. with gentle shaking. Reaction progress was monitored by MALDI-TOF MS or ESI-TOF MS, and if starting material remained after 18 h another portion of FUT5 was added until no starting material could be detected. The reaction mixture was centrifuged over a Nanosep® Omega ultrafiltration device (10 kDa MWCO) to remove reaction proteins and the filtrate was lyophilized. Purification by HILIC HPLC (sec section 2f) or P2 size-exclusion column chromatography provided the desired product.

General Procedure for the Installation of α2,3 Neu5Ac Using ST3GAL4

Glycosyl asparagine acceptor (1 eq) and CMP-Neu5Ac (1.5 eq) were dissolved at a final acceptor concentration of 2-5 mM in a sodium cacodylate buffered solution (50 mM, pH 7.2) containing BSA (1% total volume). CIAP (1% volume total) and ST3GAL4 (1% wt/wt relative to acceptor substrate) were added, and the reaction mixture was incubated overnight at 37° C. with gentle shaking. Reaction progress was monitored by ESI-TOF MS, and if starting material remained after 18 h another portion of ST3GAL4 was added until no starting material could be detected. The reaction mixture was centrifuged over a Nanosep® Omega ultrafiltration device (10 kDa MWCO) to remove reaction proteins, and the filtrate was lyophilized. Purification by HILIC HPLC (see section 2f) or P2 size-exclusion column chromatography provided the desired product.

General Procedure for the Selective Installation of Terminal α2,6 Neu5Ac Using ST6GAL1

Glycosyl asparagine (1 cq) and CMP-Neu5Ac (1.1 eq) were dissolved at a final acceptor concentration of 2-5 mM in a sodium cacodylate buffered solution (100 mM, pH 6.5) containing BSA (1% volume total). CIAP (1% volume total) and ST6GAL1 (1% wt/wt relative to acceptor substrate) were added, and the reaction mixture was incubated overnight at 37° C. with gentle shaking. The reaction mixture was centrifuged over a Nanosep® Omega ultrafiltration device (10 kDa MWCO) to remove reaction proteins, and the filtrate was lyophilized. Purification by HILIC HPLC (see section 2f) or P2 size-exclusion column chromatography provided the desired product.

General Procedure for the Selective Cleavage of Galactose Using *E. coli* β-Galactosidase[10]

Glycosyl asparagine was dissolved at a concentration of 5 mM in a Tris buffered solution (50 mM, pH 7.3) containing 5 mM $MgCl_2$. To this solution was added 50 U/μmol glycosyl asparagine of *E. coli* β-galactosidase (Sigma-Aldrich #, G5635) and the mixture was incubated overnight at 37° C. The reaction mixture was centrifuged using a Nanosep® Omega ultrafiltration device (10 kDa MWCO) to remove the enzyme and the filtrate was lyophilized Purification by HILIC HPLC (see section 2f) or P2 size-exclusion column chromatography provided the desired product.

General Procedure for Removal of TFA Protecting Group of an N-Glycan. The GlcNTFA moiety of S6 was converted to $GlcNH_2$ by dissolving the substrate (3.8 mg, 1.8 μM) in $H_2O$ to a final concentration of 10 mM. The pH of the solution was adjusted to 10 using μL aliquots 1 M NaOH. The reaction mixture was incubated overnight at 37° C. with gentle shaking. Progress of the reaction was monitored by MALDI-TOF MS and once complete the solvent was removed by lyophilization. The reaction was neutralized by μL aliquots of 1 M acetic acid and purified by P2 size-exclusion chromatography eluting with 50 mM ammonium bicarbonate to yield the desired target 2 as a white fluffy solid (3.5 mg, 92%).

General Procedure for the Conversion of $GlcNH_2$ to $GlcN_3$. Substrate 15 (9.3 mg, 5 μmol, 1 eq) was dissolved in water (1.6 mL) and to this solution was added imidazole-1-sulfonyl azide hydrogen sulfate (13.4 mg, 50 μmol), $K_2CO_3$ (6.8 mg, 50 μmol) and catalytic $CuSO_4·5H_2O$. The reaction mixture was incubated overnight at 37° C. with gentle shaking. Reaction progress was monitored by MALDI-TOF MS and if starting material remained, an additional ½ portion of the imidazole-1-sulfonyl azide hydrogen sulfate, $K_2CO_3$, and $CuSO_4$ was added until no starting material could be observed. The reaction solvent was removed by lyophilization and the salts were removed by P2 size-exclusion chromatography eluting with 50 mM ammonium bicarbonate to yield 23 as a white fluffy solid (7.2 mg. 76%).

General procedure for reduction of $GlcN_3$. Intermediate 27 (2.3 mg, 0.66 μmol, 1 eq) was dissolved in a solution of 9:1 pyridine/triethylamine to give a final concentration of 5 mM. The mixture was vortexed until all solids dissolved and 10 eq. 1,3-dithiolpropane (0.7 mg, 6.6 μmol, 10 eq) were added in one portion. The reaction mixture was kept at 37° C. was until no azide could be detected by ESI-TOF-MS. Reaction was carried forward to acetylate the amine without further purification.

General Procedure for Amine Acetylation. 18 (1.3 mg, 0.5 μmol, 1 eq) was dissolved in water to a final concentration of 2 mM. The pH was adjusted to 8 using μL aliquots of 1M NaOH. To this solution was added solid AcOSu (0.7 mg, 5 μmol, 10 eq) in one portion. The reaction mixture was vortexed vigorously until all solids were dissolved. The reaction was kept at 37° C. until full acetylation was observed by ESI-TOF-MS. In the event starting amine was detected, additional AcOSu (5 eq) was added until complete conversion was observed. The reaction was lyophilized and purified by HPLC using a HILIC column (supporting information 2f) to afford 19 as a white fluffy solid (0.9 mg, 67%).

2f. General Protocols for HILIC-HPLC Purification

HILIC-HPLC Purification Conditions for Glycosyl Asparagine Targets

Semi-preparative HILIC-HPLC was performed on a Shimadzu LC-ESI-IT-TOF with a Waters XBridge BEH, Amide column, 5 μm, 10×250 mm at a flow rate of 2.3 mL/min, injection volume of 100 μL (10-20 mg/mL), with 1% of the flow is diverted to the ESI-MS detector using a splitter. Mobile phase A was 10 mM ammonium formate in water, adjusted to pH 4.5 with formic acid; mobile phase B was 90% acetonitrile with 10% 10 mM ammonium formate in water (pH=4.5). The general condition using a linear gradient is as follows:

| Time (min) | A (%) | B (%) |
|---|---|---|
| 0 | 20 | 80 |
| 40 | 55 | 45 |
| 45 | 80 | 20 |
| 55 | 20 | 80 |
| 60 | 20 | 80 |

1 was purified using a linear gradient with the following conditions:

| Time (min) | A (%) | B (%) |
|---|---|---|
| 0 | 20 | 80 |
| 60 | 40 | 60 |
| 70 | 50 | 50 |
| 71 | 80 | 20 |
| 80 | 80 | 20 |
| 85 | 20 | 80 |
| 90 | 20 | 80 |

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A compound represented by the following structural formula:

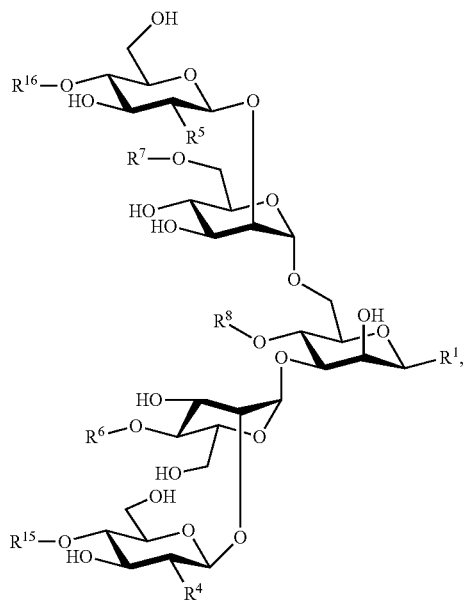

or a pharmaceutically acceptable salt thereof, wherein:
$R^1$ is OH or a residue represented by the following structural formula:

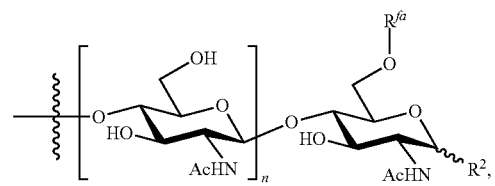

wherein:
n is 1 or 0;
$R^{fa}$ is H or a fucose residue represented by the following formula:

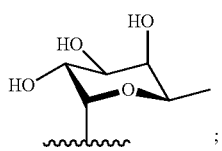

and
$R^2$ is $OR^c$, $NR^{2n}OR^c$, or $NR^{2a}R^c$, wherein $R^{2n}$ is H or a $C_{1-4}$ alkyl, and $R^c$ is H, or a $C_{1-8}$ alkyl;
$R^4$ is $N_3$ or $NR^{4a}R^{4b}$, wherein $R^{4a}$ and $R^{4b}$, each independently, is H or $Z-X^4$, wherein Z is null, C=O, $SO_2$, and $X^4$ is $C_{1-4}$alkyl or $C_{1-4}$haloalkyl;
$R^5$ is $N_3$ or $NR^{5a}R^{5b}$, wherein $R^{5a}$ and $R^{5b}$, each independently, is H or $Z-X^5$, wherein Z is null, C=O, $SO_2$, and $X^4$ is $C_{1-4}$alkyl or $C_{1-4}$haloalkyl
$R^6$ is hydrogen or a residue represented by the following formula:

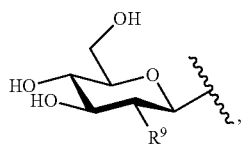

wherein R⁹ is N₃ or NR⁹ᵃR⁹ᵇ, wherein R⁹ᵃ and R⁹ᵇ, each independently, is H or Z—X⁹, wherein Z is null, C=O, SO₂, and X⁹ is $C_{1-4}$alkyl or $C_{1-4}$haloalkyl;

R⁷ is hydrogen or a residue having the formula:

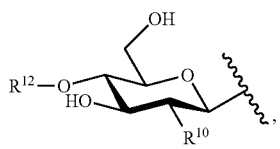

wherein:

R¹⁰ is N₃ or NR¹⁰ᵃR¹⁰ᵇ, wherein R¹⁰ᵃ and R¹⁰ᵇ, each independently, is H or Z—X¹⁰, wherein Z is null, C=O, SO₂, and X⁴ is $C_{1-4}$alkyl or $C_{1-4}$haloalkyl; and R¹² is hydrogen or a residue represented by the formula:

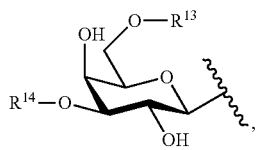

wherein:

R¹³ is hydrogen or a residue represented by the formula:

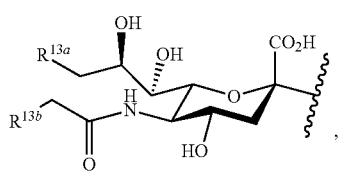

wherein R¹³ᵇ is H and R¹³ᵃ is OH;

R¹⁴ is hydrogen or a residue having the formula:

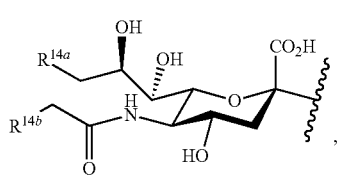

wherein R¹⁴ᵇ is H and R¹⁴ᵃ is OH;

R⁸ is hydrogen or a residue represented by the following formula:

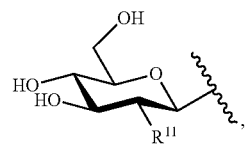

wherein

R¹¹ is N₃ or NR¹¹ᵃR¹¹ᵇ, wherein R¹¹ᵃ and R¹¹ᵇ, each independently, is H or Z—X¹¹, wherein Z is null, C=O, SO₂, and X¹¹ is $C_{1-4}$alkyl or $C_{1-4}$haloalkyl;

R¹⁵ is hydrogen or a residue represented by the following formula:

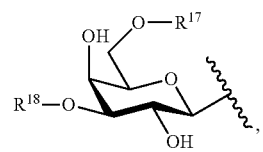

wherein:

R¹⁷ is hydrogen or a residue represented by the following formula:

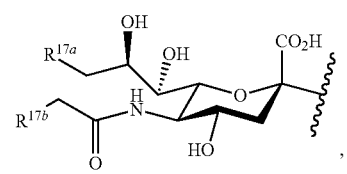

wherein R¹⁷ᵇ is H and R¹⁷ᵃ is OH;

R¹⁸ is hydrogen or a residue having the formula:

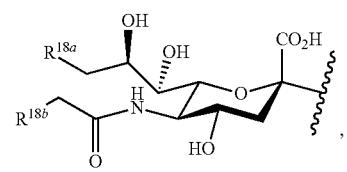

wherein R¹⁸ᵇ is H and R¹⁸ᵃ is OH; and

R¹⁶ is hydrogen or a residue represented by the following formula:

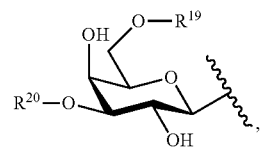

wherein R¹⁹ is hydrogen or a residue represented by the following formula:

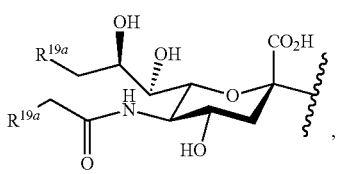

wherein $R^{19b}$ is H, and $R^{19a}$ is OH;

$R^{20}$ is hydrogen or a residue having the formula:

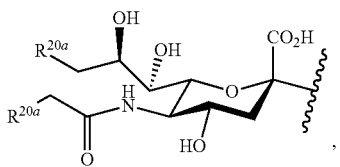

wherein $R^{20b}$ is H and $R^{20a}$ is OH.

2. The compound of claim 1, wherein:

n is 1;

$R^{fa}$ is H or a fucose residue represented by the following formula:

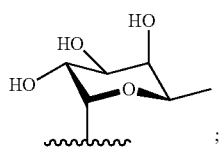

and $R^2$ is OH.

3. The compound of claim 1, wherein $R^4$ is $NH_2$.

4. The compound of claim 1, wherein $R^5$ is $NH_2$.

5. The compound of claim 1, wherein each of $R^6$, $R^7$, and $R^8$ is hydrogen.

6. The compound of claim 1, wherein each of $R^{15}$ and $R^{16}$ is hydrogen.

7. The compound of claim 1, wherein $R^{15}$ is a residue represented by the following formula:

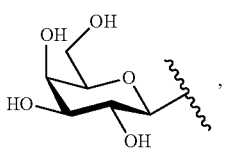

8. The compound of claim 1, wherein $R^{15}$ is the residue represented by the following formula:

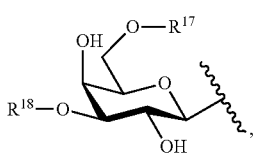

9. The compound of claim 8, wherein $R^{17}$ is a residue represented by the following formula:

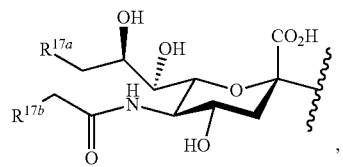

wherein $R^{17b}$ is H and $R^{17a}$ is OH.

10. The compound of claim 8, wherein $R^{18}$ is a residue having the formula:

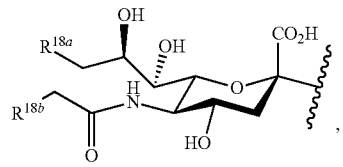

wherein $R^{18b}$ is H and $R^{18a}$ is OH.

11. The compound of claim 1, wherein $R^{16}$ is a residue represented by the following formula:

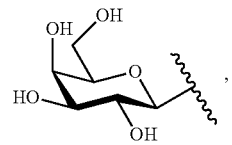

12. The compound of claim 1, wherein $R^{16}$ is a residue represented by the following formula:

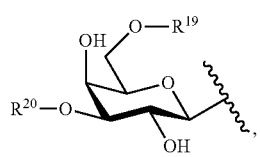

13. The compound of claim 12, wherein $R^{19}$ is a residue represented by the following formula:

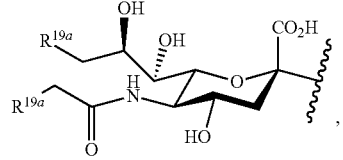

wherein $R^{19b}$ is H, and $R^{19a}$ is OH.

14. The compound of claim 12, wherein $R^{20}$ is a residue having the formula:

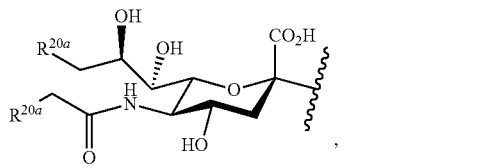
wherein $R^{20b}$ is H and $R^{20a}$ is OH.
15. The compound of claim 1, wherein $R^4$ is $NR^{4a}R^{4b}$, wherein $R^{4a}$ and $R^{4b}$, each independently, is H or Z—$X^4$, wherein Z is null and $X^4$ is $C_{1-4}$alkyl.
16. The compound of claim 1, wherein $R^5$ is $NR^{5a}R^{5b}$, wherein $R^{5a}$ and $R^{5b}$, each independently, is H or Z—$X^5$, wherein Z is null and $X^4$ is $C_{1-4}$alkyl.
* * * * *

UNITED STATES PATENT AND TRADEMARK OFFICE
CERTIFICATE OF CORRECTION

PATENT NO. : 12,152,053 B2  
APPLICATION NO. : 18/240621  
DATED : November 26, 2024  
INVENTOR(S) : Geert-Jan Boons, Anthony Robert Prudden and Lin Liu Page 1 of 1

It is certified that error appears in the above-identified patent and that said Letters Patent is hereby corrected as shown below:

In the Claims

Column 64, Claim 1, Line 58, reading:  
$R^2$ is $OR^c$, $NR^{2n}OR^c$, or $NR^{2a}R^c$, wherein $R^{2n}$ is H or Should read:  
$R^2$ is $OR^c$, $NR^{2n}OR^c$, or $NR^{2n}R^c$, wherein $R^{2n}$ is H or Signed and Sealed this  
Eleventh Day of February, 2025

Coke Morgan Stewart  
*Acting Director of the United States Patent and Trademark Office*